US010569007B2

(12) United States Patent
Hobro et al.

(10) Patent No.: US 10,569,007 B2
(45) Date of Patent: Feb. 25, 2020

(54) DIALYSIS SYSTEM AND METHOD INCLUDING A FLOW PATH INSULATOR

(71) Applicant: GAMBRO LUNDIA AB, Lund (SE)

(72) Inventors: Sture Hobro, Lund (SE); Olof Jansson, Vellinge (SE); Erik Torgny, Lund (SE); Peter Sendelius, Staffanstorp (SE); Ingemar Palsson, Lund (SE); Daniel Stahl, Eslov (SE)

(73) Assignee: GAMBRO LUNDIA AB, Lund (SE)

( * ) Notice: Subject to any disclaimer, the term of this patent is extended or adjusted under 35 U.S.C. 154(b) by 113 days.

(21) Appl. No.: 15/765,806

(22) PCT Filed: Oct. 14, 2016

(86) PCT No.: PCT/EP2016/074712
§ 371 (c)(1),
(2) Date: Apr. 4, 2018

(87) PCT Pub. No.: WO2017/064252
PCT Pub. Date: Apr. 20, 2017

(65) Prior Publication Data
US 2018/0280604 A1    Oct. 4, 2018

(30) Foreign Application Priority Data

Oct. 14, 2015  (SE) ...................... 1551323

(51) Int. Cl.
*A61M 1/34*  (2006.01)
*A61M 1/36*  (2006.01)
(Continued)

(52) U.S. Cl.
CPC ............. *A61M 1/367* (2013.01); *A61M 1/14* (2013.01); *A61M 1/16* (2013.01); *A61M 1/34* (2013.01);
(Continued)

(58) Field of Classification Search
None
See application file for complete search history.

(56) References Cited

U.S. PATENT DOCUMENTS

| 4,155,852 A | 5/1979 | Fischel et al. |
| 4,443,333 A | 4/1984 | Mahurkar |

(Continued)

FOREIGN PATENT DOCUMENTS

| DE | 3512533 | 10/1986 |
| EP | 0458041 | 11/1991 |

(Continued)

OTHER PUBLICATIONS

Notice of Opposition filed by Fresenius Medical Care AC & Co. KGaA in related EP Patent Application No. 2616117B1 on Sep. 9, 2016.

(Continued)

*Primary Examiner* — Chester T Barry
(74) *Attorney, Agent, or Firm* — K&L Gates LLP

(57) ABSTRACT

A renal failure therapy system (10) includes: a dialyzer (102); a blood circuit (100) including a blood pump (120) in fluid communication with the dialyzer (102); a dialysis circuit (30) in fluid communication with the dialyzer (102); and at least one flow path insulator (150, 155) located in the dialysis circuit (30) or the blood circuit (100), the flow path insulator (150, 155) including a structure that separates liquid flowing within the flow path insulator (150, 155) into a plurality (e.g., two or more) of separated liquid segments (160) that create electrical isolation within the flow path insulator (150, 155).

27 Claims, 15 Drawing Sheets

(51) Int. Cl.
*A61M 1/16* (2006.01)
*A61M 1/14* (2006.01)

(52) U.S. Cl.
CPC ........ *A61M 1/3413* (2013.01); *A61M 1/3621* (2013.01); *A61M 2205/07* (2013.01); *A61M 2205/15* (2013.01); *A61M 2205/3306* (2013.01); *A61M 2205/3331* (2013.01); *A61M 2205/3334* (2013.01); *A61M 2205/3368* (2013.01); *A61M 2205/3372* (2013.01); *A61M 2205/70* (2013.01); *A61M 2206/14* (2013.01)

(56) References Cited

U.S. PATENT DOCUMENTS

| | | | |
|---|---|---|---|
| 5,578,223 | A | 11/1996 | Bene et al. |
| 5,736,038 | A | 4/1998 | Stoughton |
| 6,136,201 | A | 10/2000 | Shah et al. |
| 8,180,443 | B1 | 5/2012 | Kleinekofort et al. |
| 2003/0195453 | A1 | 10/2003 | Han et al. |
| 2003/0209475 | A1 | 11/2003 | Connell et al. |
| 2003/0218623 | A1 | 11/2003 | Krensky et al. |
| 2003/0220598 | A1 | 11/2003 | Busby et al. |
| 2004/0019312 | A1 | 1/2004 | Childers et al. |
| 2004/0267183 | A1 | 12/2004 | Chevallet |
| 2005/0045540 | A1 | 3/2005 | Connell et al. |
| 2005/0090774 | A1 | 4/2005 | Tonelli et al. |
| 2005/0131332 | A1 | 6/2005 | Kelly et al. |
| 2006/0177351 | A1 | 8/2006 | Heiniger et al. |
| 2008/0065006 | A1 | 3/2008 | Roger et al. |
| 2009/0177149 | A1 | 7/2009 | Childers et al. |
| 2009/0287134 | A1 | 11/2009 | Hildwein et al. |
| 2010/0022935 | A1 | 1/2010 | Muller |
| 2010/0312161 | A1 | 12/2010 | Jonsson et al. |
| 2013/0158469 | A1* | 6/2013 | Hopping ............... A61M 1/28 604/28 |
| 2013/0319920 | A1* | 12/2013 | Hansson ............... A61M 1/14 210/143 |
| 2014/0228803 | A1 | 8/2014 | Kogan |

FOREIGN PATENT DOCUMENTS

| | | |
|---|---|---|
| EP | 0611228 | 8/1994 |
| EP | 0820776 | 1/1998 |
| GB | 927349 | 5/1963 |
| JP | 1024102 | 1/1998 |
| JP | 1085323 | 4/1998 |
| WO | 9306875 | 4/1993 |
| WO | 9411093 | 5/1994 |
| WO | WO2005044339 | 5/2005 |
| WO | 2008031539 | 3/2008 |
| WO | 2009044220 | 4/2009 |
| WO | 2010011441 | 1/2010 |
| WO | 2010077762 | 7/2010 |

OTHER PUBLICATIONS

Eidesstattliche Versicherung von Herrn Dr. Jorg Dreyhsig. Affidavit of Dr. Jorg Dreyhsig asserting the booklet referred to as D13 (Fresenius Medical Care: Prospekt: Acute Therapy Systems: multiFiltrate, 2006) was available to the public at the ERA-EDTA conference in Glasgow, UK in 2006. D13.
DIN EN 60601-1 (VDE 0750-1), Seiten 84-87 (Jul. 2007). Medical electrical equipment—Part 1 : General requirements for basic safety and essential performance (IEC 60601-1 :2005); German version EN 60601-1:2006. D16.
C. Ronco et al., "Critical Care Nephrology," Kluwer Academic Publishers, 1998. 7 pages. D12.
Ansiiaami ES1-1993. American National Standard. Current safe limits for electromedical apparatus. Developed by Association for the Advancement of Medical Instrumentation. Dec. 2, 1993. D15.
Jonsson et al., "Blood lines conduct leakage current during haemodialysis: a potential safety risk during first failure, especially for patients with central dialysis catheter as access", Med. Bioi. Eng. Comput., 2005, 43, 731-738, 8 total pages.
Non-Final Office Action issued in U.S. Appl. No. 13/824,892 dated Jul. 14, 2016.
Final Office Action issued in U.S. Appl. No. 13/824,892 dated Jan. 25, 2017.
Non-Final Office Action issued in U.S. Appl. No. 13/824,892 dated Jul. 11, 2017.
Response to the Non-Final Office Action dated Jul. 11, 2017 in U.S. Appl. No. 13/824,892. Response dated Nov. 8, 2017.
Final Office Action issued in U.S. Appl. No. 13/824,892 dated Feb. 22, 2018.
International-Type Search Report issued in related Swedish Patent Application No. SE1551323-7 dated May 4, 2016.
Office Action issued in related Swedish Patent Application No. SE1551323-7 dated May 4, 2016.
International Search Report issued in International Patent Application No. PCT/EP2016/074712 dated Jan. 12, 2017.
Written Opinion issued in International Patent Application No. PCT/EP2016/074712 dated Jan. 12, 2017.

\* cited by examiner

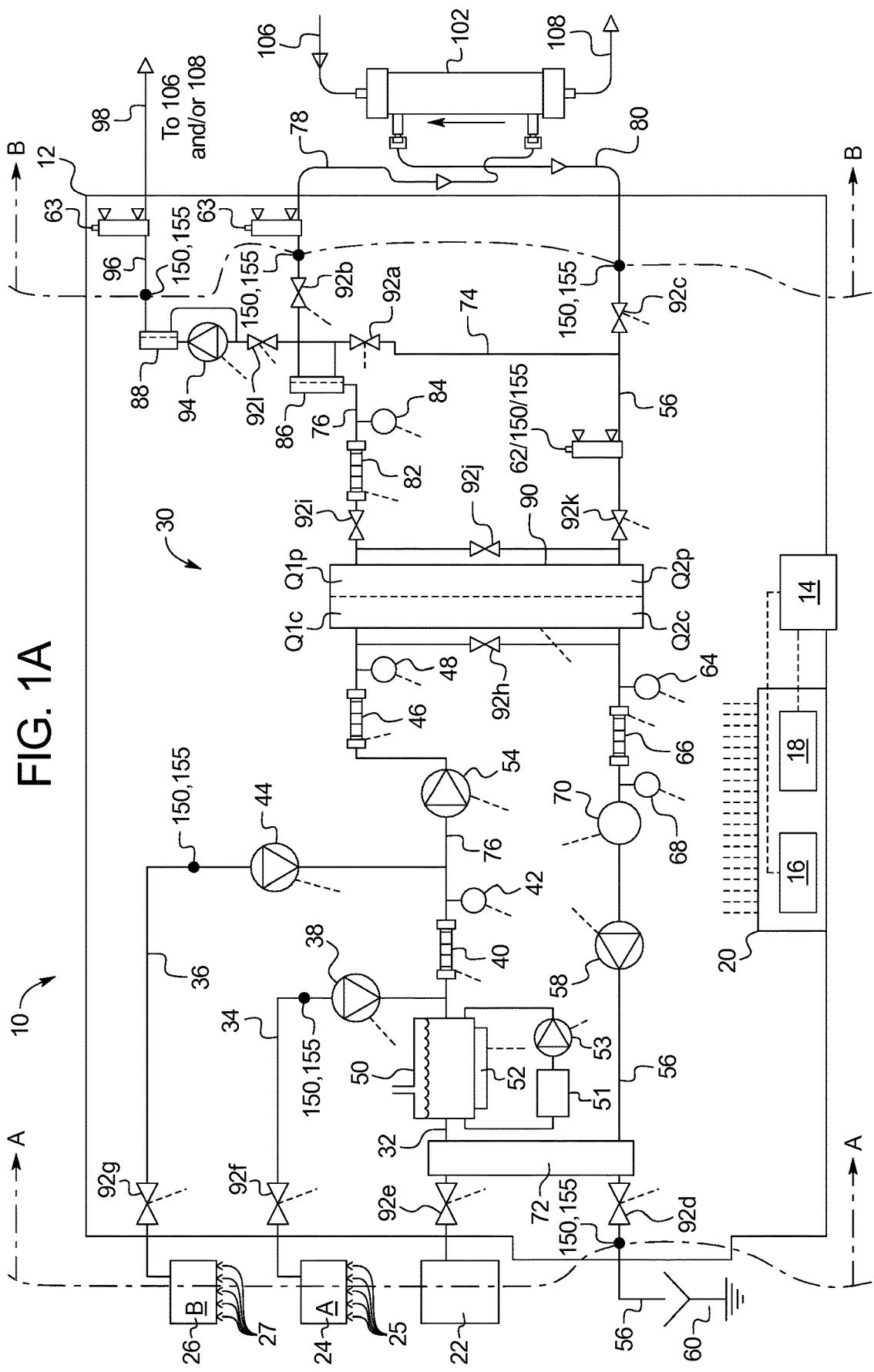

DIALYSIS SYSTEM AND METHOD INCLUDING A FLOW PATH INSULATOR

PRIORITY CLAIM

The present application is a National Phase of International Application No. PCT/EP2016/074712, filed on Oct. 14, 2016, which claims priority to Swedish Patent Application No. 1551323-7, filed on Oct. 14, 2015, the entire contents of each of which are being incorporated herein by reference.

BACKGROUND

The present disclosure relates generally to medical devices. More specifically, the present disclosure relates to the electrical insulation of medical devices.

Hemodialysis ("HD") in general uses diffusion to remove waste products from a patient's blood. A diffusive gradient that occurs across the semi-permeable dialyzer between the blood and an electrolyte solution called dialysis fluid causes diffusion. Hemofiltration ("HF") is an alternative renal replacement therapy that relies on a convective transport of toxins from the patient's blood. This therapy is accomplished by adding substitution fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism, which is particularly beneficial in removing middle and large molecules (in hemodialysis there is a small amount of waste removed along with the fluid gained between dialysis sessions, however, the solute drag from the removal of that ultrafiltrate is typically not enough to provide convective clearance).

Hemodiafiltration ("HDF") is a treatment modality that combines convective and diffusive clearances. HDF flows dialysis fluid from the dialyzer inlet to its outlet. In addition, substitution fluid is provided directly to the extracorporeal circuit, providing convective clearance. These modalities are administered by a dialysis machine. The machines may be provided in a center or in a patient's home. Dialysis machines provided in a center are used multiple times a day for multiple patients and therefore must be cleaned between treatments. Dialysis machines use multiple components, including electrical components. Electrical components pose a risk for an electrical failure. To safeguard the patient against an internal failure of the dialysis machine's flow path, today's dialyze machines are electrically grounded. Nevertheless, the patient may come in to contact with a device that is not properly grounded, such as chargers for mobile phones or laptop, electrical adjustable chairs, or even reading lamps.

Medical devices are designated into different electrical categories. Cardiac Floating "CF" machines, for example, are machines having components ("applied parts"), which come into direct conductive contact with the patient's heart. Examples of CF machines are heart lung machines, external pacemakers, electrical surgery devices, pacemakers, and defribulators. Body Floating "BF" machines have applied parts that come into conductive contact with the patient, or have medium or long term contact with the patient. Examples of BF machines include monitors, incubators and ultrasound equipment. Body ("B") machines have applied parts that are normally not conductive and may be immediately released from the patient. Examples of B machines include light emitting diode ("LED") lighting, medical lasers, MRI body scanners, hospital beds and photography equipment.

CF and BF applied parts have floating patient grounds, while B machines may be connected to earth ground. It is desirable to have a reliable and cost effective way for dialysis machines to maintain a floating patient ground, which can at least approach a BF or CF rated machine.

SUMMARY

The present disclosure provides a renal failure therapy system and method that performs hemodialysis ("HD"), hemofiltration ("HF") and hemodiafiltration ("HDF"). Accordingly, "renal failure therapy" as used herein is meant to include any one, or more, or all of HD, HF and/or HDF.

The renal failure therapy system of the present disclosure provides a flow path insulator in a concentrate, dialysis fluid and/or blood flow path. If the incoming water is sufficiently purified and deionized, no current may flow and the device of the present disclosure is not needed. The insulator includes an air gap that breaks the dialysis fluid or blood flow into a discontinuous, drop type flow, which in turn breaks an electrical pathway residing in the concentrate, dialysis fluid or blood. The insulator may include an air pump and a sensor, wherein the sensor senses a liquid level in the insulator and sends a signal indicating the same to a controller, which uses the signal to control the air pump. The air pump regulates the liquid/air interface to a desired level. In an alternative embodiment, the a liquid pump, such as a concentrate pump, dialysis fluid pump or blood pump receives the level sensor feedback to regulate the liquid/air interface to a desired level.

Discussed in detail herein are various ways to obtain and maintain the discontinuous or drop type flow. In one embodiment, a valve is pulsed on a regular basis to produce short streams of flow that are not long enough to create an electrical continuity between liquid in the valve and the liquid within the insulator. To increase flowrate, two or more pulsed valve outlets are provided in the insulator. Each pulsed valve outlet produces short streams of flow that are not long enough to create an electrical continuity between liquid in the valve and the liquid within the insulator. The pulsed valve outlets are spaced far enough from each other, such that their streams are separate and may not be combined to produce electrical continuity.

In another embodiment, a turbine wheel is employed. The turbine wheel is in one embodiment driven by the liquid flow entering the insulator. The turbine includes paddles, blades or vanes that are contacted by the incoming liquid. The incoming liquid spins the paddles, blades or vanes of the turbine wheel, which in turn break the incoming liquid into discontinuous segments that fall to the liquid/air interface within the device and at the same time break electrical continuity within the device.

In a third embodiment, the incoming liquid is sprayed through a shower or manifold head having many small openings that break the flow into a shower of discontinuous drop flows. In a fourth embodiment, the shower or manifold head is combined with the turbine wheel, wherein the turbine wheel intermittently blocks the smaller holes of the shower head to create many discontinuous, drop type streams.

In a fourth embodiment, the liquid inlet is at least substantially horizontal and directed along an inner wall (e.g., cylindrical wall) of the insulator. The horizontally directed liquid forms a thin film along the wall that migrates from the top of the insulator, where the liquid inlet resides, to the liquid/air interface within the insulator. The film due to its small thickness ensures that the electrical impendence within the flow path insulator is very high.

In a fifth embodiment, a paddle wheel type structure is placed inside the flow path insulator. The paddle wheel structure may have paddles or cups that fill with liquid falling from the top of the insulator. The wheel turns due to the weight of the liquid filling one of the paddles or cups. The turning wheel causes a first paddle or cup to move out of the way, so that a second paddle or cup instead begins to fill with liquid. The different paddles or cups separate the liquid and break electrical continuity. The wheel turns so that each paddle or cup discharges its liquid into the liquid bath within the insulator, resetting the paddle or cup for its next liquid load.

Any of the above-discussed embodiments, except perhaps the thin film embodiment, may be provided with an air isolation area or chamber, which is located at the top of the insulator where the liquid is introduced. The air isolation area isolates the liquid inlet into the insulator from adverse effects building within the flow path insulator over time. It is expected that as the insulator is used over the course of a treatment or over the course of multiple treatments, the inner surface of the insulator will become wet and coated possibly with biological or salt deposits from the concentrate or the dialysis fluid. Such conductive coating may provide an undesired electrical path to ground. Also, if the atmosphere within the insulator turns humid, creating a salty conductive fog, a disruptive discharge may appear between the drops or liquid segments, causing another undesired path to ground.

Various embodiments are shown and discussed below for creating the liquid segments in combination with the use of an air isolation chamber. In one implementation, a first air line and pump are provided to supply the air isolation chamber, while a second air line and pump are provided to pull air into the liquid line to create the segments. In another implementation, an air line and pump are provided to supply the air isolation chamber, while a valve is used to split the liquid flow into segments. The valve may be a two- or three-way valve. The valve may also be used in combination with an upstream compliance chamber that holds a varying volume of the liquid as the valve cycles. In a further implementation, an air line and pump are provided to supply the air isolation chamber, while a motor is used to turn a flange that sequentially allows and disallows fluid flow, creating the fluid segments.

The air isolation chamber combats the above-described unwanted paths to ground by providing a small isolation area at the liquid inlet. The insulator or circuit working with the insulator includes an air pump that pumps air into the isolation area or chamber in one embodiment, which (i) prevents the biological or salt deposits from building in the isolation area and (ii) lowers the overall humidity within the insulator. Result (i) breaks an unwanted current path due to the biological or salt deposit film. Result (ii) helps to prevent a disruptive discharge from appearing between the drops or fluid segments.

The dialysis fluid and/or blood circuit may provide one or more of any of the flow path insulators described herein as needed to prevent a fault current, developed for example by faulty electrical equipment outside the dialysis machine touching the patient, from flowing to or from the patient. It is contemplated to use the flow path insulators additionally as drip chambers, e.g., in the blood circuit. The fresh dialysis fluid line of the dialysis circuit may contain a flow path insulator between the furthest most downstream flow component and the dialyzer, while the used dialysis fluid line of the dialysis circuit may contain a flow path insulator between the furthest most upstream flow component and the dialyzer. A flow path insulator may alternatively or additionally be placed in the most downstream portion of the used dialysis fluid line, just before the drain. Further alternatively or additionally, any of the flow path insulators described herein may be placed in a drain line external to the housing of the dialysis machine.

Moreover, the flow path insulators may be used in combination with an electrically floating fluid blood, dialysis fluid, concentrate and water (if conductive or non-deionized) pathway. Generally, an electrically floating fluid pathway is one that is not connected to earth ground. As used herein, floating fluid pathway in one embodiment means instead that there is no pathway to ground within the blood lines, dialysis fluid lines either inside or outside of the renal failure therapy machine, concentrate lines, or even the water lines if non-deionized. That is, floating fluid pathway may mean a fluid pathway which, when carrying an electrically conductive fluid therein, would itself render the conductive fluid electrically floating relative to an electrical potential, such as ground, provided to the dialysis machine through the mains and/or through grounded parts connected to the dialysis machine (e.g. drain and external water lines). The floating fluid pathway may include the entire or one or several portion(s) of the blood lines, (fresh and/or used) dialysis fluid lines, concentrate lines, and/or water lines as well as components, such as sensors and pumps, connected to the above mention fluid lines. The only pathway to ground is via the used dialysis fluid traveling outside to earth ground at the clinic's house drain. Making any fault voltages generated at the patient travel all the way to earth ground at the house drain increases the naturally occurring impedances within the fluid lines that the fault voltage sees, thereby minimizing the current generated by the fault voltage.

The flow path insulators in combination with the electrically floating fluid pathways provide electrical insulation suitable for use with a central venous catheter ("CVC"). A central venous catheter can be a long, fine catheter inserted via a large vein into the patient's superior vena cava or right atrium to withdrawl and deliver blood, e.g., for hemodialysis, or administer parenteral fluids (as in parenteral nutrition), antibiotics, or other therapeutic agents. CVC's create a more serious situation because the catheter tips are placed close to the patient's heart. Fault currents from the dialysis machine are possible. Even more likely, however, is a fault current from a source that the patient touches, e.g., from a faulty charger plugged into a computer, telephone, or tablet. If such a situation occurs, and the machine provides an electrical pathway from the blood or the blood and dialysis fluid to ground, then the outside fault may be focused through the CVC catheters near the patient's heart, through the blood or blood and dialysis fluid to earth ground. The flow path insulators in combination with the electrically floating fluid pathways prevent the above situation from occurring.

The system and method of the present disclosure also include multiple ways to test whether the flow path insulators are working correctly. For example, with flow path insulators that produce drops or liquid segments, it is contemplated to place a sensor at the side of the insulator to ensure that the discontinuous stream is indeed producing drops, and that the drops or fluid segments are an appropriate distance apart from one another. The sensor may for example be an optical sensor in which a beam of light is broken by the drops or liquid segments. The optical sensor alternatively includes one or more camera. If the sensor is placed close enough to the continuous stream, it may be possible to use ultrasonic, capacitive or inductive sensors alternatively.

Alternatively or additionally to the sensor, it is contemplated to test whether the flow path insulators are working correctly by providing an electrical path to ground from the dialysis circuit for example, which is separated by a switch, a current generator, and a voltage meter. The switch in one embodiment is a three position switch with fluid path (analogous to line), disconnected (analogous to neutral) and ground positions. In the fluid path (analogous to line) position, the voltage meter reads voltage generated by the current generator. In the disconnected (analogous to neutral) position, the current generator is disconnected from the dialysis circuit, while the voltage meter may still read a voltage in the fluid or dialysis fluid pathway. In the ground position, the voltage that the voltage meter sees is any fault voltage through the dialysis fluid pathway to earth ground.

In an embodiment, prior to the patient being connected to the machine, the three position switch is connected to earth ground to look for a fault voltage indicating that the flow path insulator or the electrically floating pathway is not operating properly. If that test is passed, and before the patient is connected, the switch is changed to the fluid path (analogous to line) position, where the voltage due to the current source is detected. In an embodiment, the current source is set to a maximum allowable limit for a cardiac floating machine or a body floating machine, e.g., ten to fifty microamperes (A). The corresponding voltage is then measured. During treatment, when the patient is connected to the machine, the switch is switched to the disconnected (analogous to neutral) position, so that there is no path to earth ground via the switch and the current generator does not generate current in the fluid pathway. The voltage detector may still look for voltages, however, and if a voltage sensed reaches or exceeds the maximum allowable voltage (or an engineering factor thereof), then the machine may alarm and shut down, taking corrective actions such as clamping the blood lines.

In light of the technical features set forth herein, and without limitation, in a first aspect, a renal failure therapy system includes: a dialyzer; a blood circuit including a blood pump in fluid communication with the dialyzer; a dialysis circuit in fluid communication with the dialyzer; and at least one flow path insulator located in the dialysis circuit or the blood circuit, the flow path insulator including (i) a structure that separates liquid flowing within the flow path insulator into a plurality (e.g., two or more) separated liquid segments that create electrical isolation within the flow path insulator, and (ii) an air isolation chamber that is separated by at least one baffle from a lower chamber that receives the liquid segments to keep the air isolation chamber dry.

In a second aspect, which may be used with any other aspect described herein unless specified otherwise, the flow path insulator includes an air isolation chamber that is that is separated by at least one baffle (201) from a lower chamber that receives the liquid segments to keep the air isolation chamber dry.

In a third aspect, which may be used with any other aspect described herein unless specified otherwise, the flow path insulator is configured and arranged to use a flow of separated liquid segments to pull air through the air isolation chamber.

In a fourth aspect, which may be used with any other aspect described herein unless specified otherwise, the flow path insulator includes an inlet, wherein the air isolation chamber surrounds the inlet, and which further includes an air pump positioned and arranged to pressurize air within the isolation chamber, or which is configured to draw in air itself.

In a fifth aspect, which may be used with any other aspect described herein unless specified otherwise, the structure that separates liquid flowing within the flow path insulator into liquid segments includes at least one valve opened and closed sequentially to create the liquid segments.

In a sixth aspect, which may be used with the first four aspects and any aspect subsequent to the eighth aspect unless specified otherwise, the structure that separates liquid flowing within the insulator into liquid segments includes a turbine wheel including blades that are spun by the flowing liquid.

In a seventh aspect, which may be used with the first four aspects and any aspect subsequent to the eighth aspect unless specified otherwise, the structure that separates liquid flowing within the insulator into liquid segments includes a manifold plate defining a plurality of apertures, each aperture restricting the flowing liquid.

In an eighth aspect, which may be used with the first four aspects and any aspect subsequent to this aspect, the structure that separates liquid flowing within the insulator into liquid segments includes a wheel having a plurality of receptacles that fill individually, wherein the weight of the filled receptacles causes the wheel to turn.

In a ninth aspect, which may be used with any other aspect described herein unless specified otherwise, the system includes a logic implementer, wherein the flow path insulator includes a level sensor configured to send an output to the logic implementer, the logic implementer using the output to control an air pump to achieve a desired liquid level in the insulator.

In a tenth aspect, which may be used with any other aspect described herein unless specified otherwise, the system includes at least one testing apparatus for testing whether the flow path insulator is operating properly.

In an eleventh aspect, which may be used with the tenth aspect in combination with any other aspect described herein unless specified otherwise, the at least one testing apparatus includes a sensor positioned and arranged to sense whether the fluid segments are being formed properly.

In a twelfth aspect, which may be used with the tenth aspect in combination with any other aspect described herein unless specified otherwise, the at least one testing apparatus includes a voltage or current meter positioned and arranged to detect voltage or current in the dialysis circuit.

In a thirteenth aspect, which may be used with any other aspect described herein unless specified otherwise, the dialysis circuit includes a fresh dialysis fluid line and a used dialysis fluid line, and which includes a first flow path insulator located in the fresh dialysis fluid line and a second flow path insulator located in the used dialysis fluid line.

In a fourteenth aspect, which may be used with the thirteenth aspect in combination with any other aspect described herein unless specified otherwise, the first flow path insulator is located between a furthest downstream flow component in the fresh dialysis fluid line and the dialyzer, and the second flow path insulator is located between a furthest upstream flow component in the used dialysis fluid line and the dialyzer.

In a fifteenth aspect, which may be used with any other aspect described herein unless specified otherwise, the flow path insulator is placed at the drain of the dialysis circuit and/or outside of a machine housing holding the dialysis circuit.

In a sixteenth aspect, which may be used with the fifteenth aspect in combination with any other aspect described herein unless specified otherwise, at least one concentrate container is suspended off of the ground or provided with standoffs to preclude capacitive coupling with the ground.

In a seventeenth aspect, which may be used with any other aspect described herein unless specified otherwise, the flow path insulator is placed in a concentrate line of the dialysis circuit or in the blood circuit.

In an eighteenth aspect, which may be used with any other aspect described herein unless specified otherwise, the flow path insulator uses a pulsed source of air to create separated liquid segments.

In an nineteenth aspect, which may be used with any other aspect described herein unless specified otherwise, a renal failure therapy machine includes: a dialyzer; a blood circuit including a blood pump in fluid communication with the dialyzer; a dialysis circuit in fluid communication with the dialyzer; at least one flow path insulator located in the dialysis circuit, the flow path insulator including a structure that separates liquid flowing within the flow path insulator into separated liquid segments that create electrical isolation within the flow path insulator; and an air pump positioned and arranged to pressurize air within an isolation chamber of the flow path insulator.

In a twentieth aspect, which may be used with the nineteenth aspect in combination with any other aspect described herein unless specified otherwise, the flow path insulator is located at a downstream end of a drain line of the dialysis circuit.

In a twenty-first aspect, which may be used with the nineteenth aspect in combination with any other aspect described herein unless specified otherwise, the isolation chamber encompasses an area of the flow path insulator at which the liquid segments are formed.

In a twenty-second aspect, which may be used with the nineteenth aspect in combination with any other aspect described herein unless specified otherwise, the isolation chamber is spaced away from a liquid/air interface formed within the flow path insulator.

In a twenty-third aspect, which may be used with the nineteenth aspect in combination with any other aspect described herein unless specified otherwise, the isolation chamber is part of a water or water and agent cleaning loop.

In a twenty-fourth aspect, which may be used with any other aspect described herein unless specified otherwise, a renal failure therapy machine includes: a dialyzer; a blood circuit including a blood pump in fluid communication with the dialyzer; a dialysis circuit in fluid communication with the dialyzer, wherein the blood circuit, the dialyzer, and the dialysis circuit form an electrically floating fluid pathway in which the only electrical path to ground is via used dialysis fluid traveling through the machine to earth ground; and at least one flow path insulator located at a drain end of the dialysis circuit, the flow path insulator including a structure that separates liquid flowing within the flow path insulator into separated liquid segments that create electrical isolation within the flow path insulator.

In a twenty-fifth aspect, which may be used with the twenty-fourth aspect in combination with any other aspect described herein unless specified otherwise, the electrically floating fluid pathway has at least one of: (i) an electrically bypassed sensor, (ii) at least one mechanical electrically insulated fluid component, or (iii) at least one electrically isolated signal line.

In a twenty-sixth aspect, which may be used with any other aspect described herein unless specified otherwise, a renal failure therapy system includes: a dialyzer; a blood circuit in fluid communication with the dialyzer; a dialysis circuit in fluid communication with the dialyzer; a flow path insulator located in the dialysis circuit or the blood circuit, the flow path insulator configured to create electrical isolation within the flow path insulator; and at least one testing apparatus for testing whether the flow path insulator is creating electrical isolation properly.

In a twenty-seventh aspect, which may be used with the twenty-sixth aspect in combination with any other aspect described herein unless specified otherwise, the at least one testing apparatus includes a sensor positioned and arranged to sense whether the flow path insulator is forming separated electrically insulating fluid segments properly.

In a twenty-eighth aspect, which may be used with the twenty-sixth aspect in combination with any other aspect described herein unless specified otherwise, the at least one testing apparatus includes a voltage or current meter positioned and arranged to determine if the flow path insulator is creating the electrical isolation properly.

In a twenty-ninth aspect, which may be used with the twenty-eighth aspect in combination with any other aspect described herein unless specified otherwise, the at least one testing apparatus includes a switch that allows at least one of a path to a ground position before treatment to test via the voltage or current meter whether the flow path insulator is creating electrical isolation properly, or (ii) a path to a fluid path (analogous to a line) position to set a maximum voltage or current level before treatment, and a path to a disconnected (analogous to a neutral) position to test during treatment whether the flow path insulator is creating electrical isolation properly based on the maximum voltage or current level.

In a thirtieth aspect, which may be used with any other aspect described herein unless specified otherwise, a renal failure therapy system includes: a dialyzer; a blood circuit including a blood pump in fluid communication with the dialyzer; a dialysis circuit in fluid communication with the dialyzer; at least one flow path insulator located in the blood circuit, the flow path insulator including a structure that separates liquid flowing within the flow path insulator into a plurality of (e.g., two or more) separated liquid segments that create electrical isolation within the flow path insulator; and a logic implementer programmed to operate a single needle treatment, the flow path insulator located in a single blood line of blood circuit running to a patient.

In a thirty-first aspect, any of the features, functionality and alternatives described in connection with any one or more of FIGS. 1A to 12C may be combined with any of the features, functionality and alternatives described in connection with any of the other one or more of FIGS. 1A to 12C.

It is therefore an advantage of the present disclosure to provide a hemodialysis, hemofiltration or hemodiafiltration system and method having electrical insulation.

It is another advantage of the present disclosure to provide a hemodialysis, hemofiltration or hemodiafiltration system and method that actively prevents or reduces electrical currents resulting from voltages due to fault conditions.

It is a further advantage of the present disclosure to provide a hemodialysis, hemofiltration or hemodiafiltration system and method that actively prevents or reduces electrical currents resulting from voltages due to fault conditions, and which is relatively easy and cost effective to implement.

It is yet another advantage of the present disclosure to provide a hemodialysis, hemofiltration or hemodiafiltration system and method that combines active prevention of electrical currents resulting from fault conditions with an electrically floating fluid pathway.

Moreover, it is an advantage of the present disclosure to provide a hemodialysis, hemofiltration or hemodiafiltration system and method that actively prevents or reduces electrical currents resulting from voltages due to fault conditions at multiple locations in the system.

Additionally, it is an advantage of the present disclosure to provide a hemodialysis, hemofiltration or hemodiafiltration system and method that actively prevents or reduces conductive films from forming on inner walls of the flow path insulators described herein, and further reduces the humidity inside the insulators to reduce the risk of an unwanted conductive connection.

Still further, an advantage of the present disclosure is to provide one or more feedback feature to ensure that the flow path insulators described herein are functioning properly.

The advantages discussed herein may be found in one, or some, and perhaps not all of the embodiments disclosed herein. Additional features and advantages of the present invention are described in, and will be apparent from, the following Detailed Description of the Invention and the figures.

BRIEF DESCRIPTION OF THE FIGURES

FIG. 1A is a schematic illustration of one embodiment of a dialysis circuit for a renal failure therapy system using the flow path insulators of the present disclosure.

DETAILED DESCRIPTION

Figure 1B:
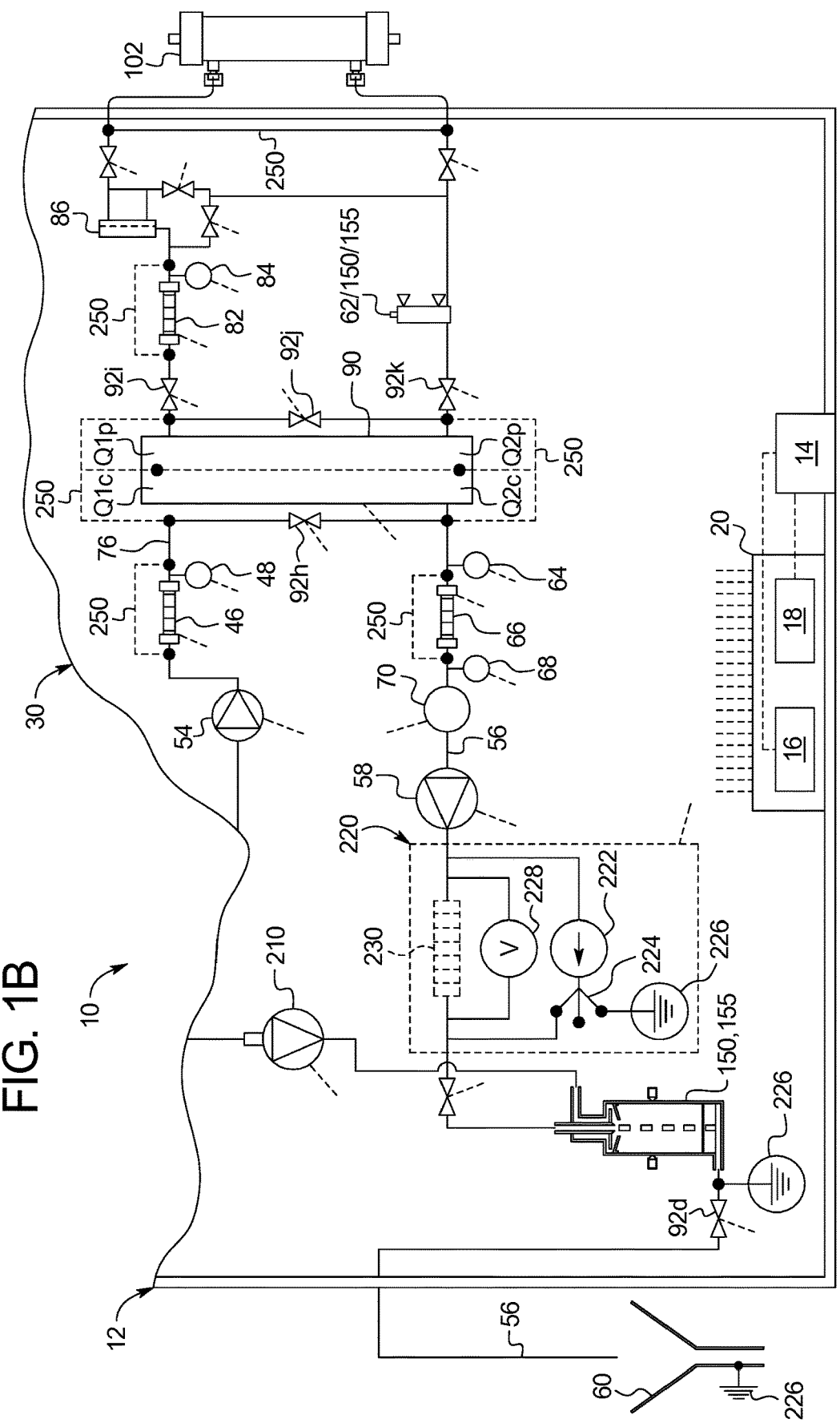
FIG. 1B is a schematic illustration of another embodiment of a dialysis circuit for a renal failure therapy system using the flow path insulators of the present disclosure in combination with an electrically floating fluid pathway, and in further combination with a feedback loop to ensure proper operation of the flow path insulators and the electrically floating fluid pathway.
Figure 2:
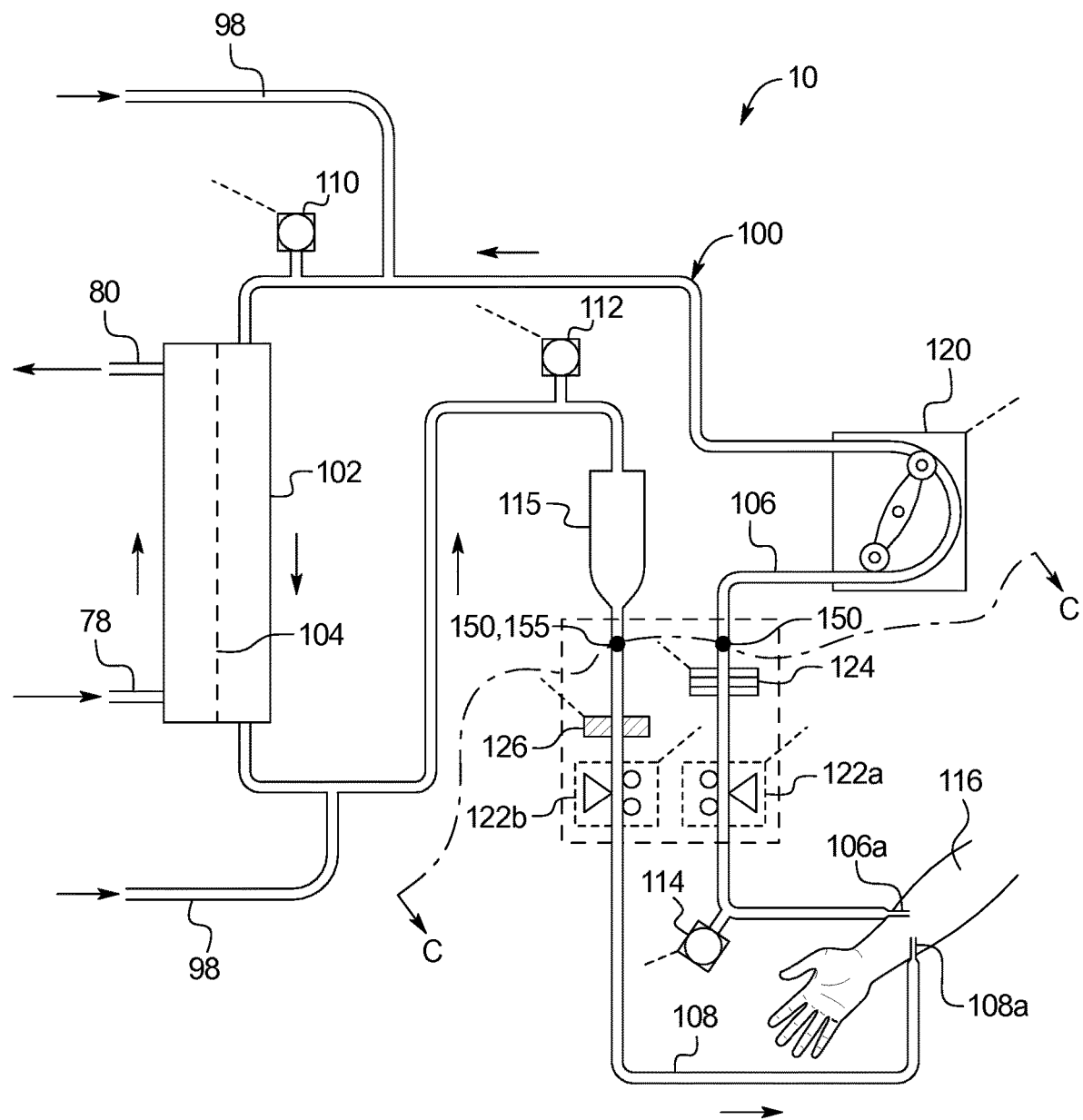
FIG. 2 is a schematic illustration of one embodiment of a blood circuit for a renal failure therapy system using a flow path insulator of the present disclosure.

Referring now to the drawings and in particular to FIGS. 1 and 2, an embodiment of a system of the present disclosure is illustrated by system 10. System 10 includes a machine 12 having an enclosure or housing. The housing of machine 12 holds the contents of a dialysis fluid or dialysis fluid circuit 30 described in detail below. The housing of machine 12 also supports a user interface 14, which allows a nurse or other operator to interact with system 10. User interface 14 may have a monitor screen operable with a touch screen overlay, electromechanical buttons, e.g., membrane switches, or a combination of both. User interface 14 is in electrical communication with at least one processor 16 and at least one memory 18. At least one processor 16 and at least one memory 18 also electronically interact with, and where appropriate, control the pumps, valves and sensors described herein, e.g., those of dialysis fluid circuit 30. At least one processor 16 and at least one memory 18 are referred to collectively herein as a logic implementer 20. The dashed lines extending from logic implementer 20 lead to pumps, valves, sensors, the heater and other electrical equipment, as indicated by like dashed lines leading from the pumps, valves, sensors, heater, etc.

Dialysis fluid circuit 30 includes a purified water line 32, an A-concentrate line 34 and a bicarbonate B-concentrate line 36. Purified water line 32 receives purified water from a purified water device or source 22. The water may be purified using any one or more process, such as, reverse osmosis, carbon filtering, ultraviolet radiation, electrodeionization ("EDI"), and/or ultrafiltering.

An A-concentrate pump 38, such as a peristaltic or piston pump, pumps A-concentrate from an A-concentrate source 24 into purified water line 32 via A-concentrate line 34.

Conductivity cell 40 measures the conductive effect of the A-concentrate on the purified water, sends a signal to logic implementer 20, which uses the signal to properly proportion the A-concentrate by controlling A-concentrate pump 38. The A conductivity signal is temperature compensated via a reading from temperature sensor 42.

A B-concentrate pump 44, such as a peristaltic or piston pump, pumps B-concentrate from a B-concentrate source 26 into purified water line 32 via B-concentrate line 36. Conductivity cell 46 measures the conductive effect of the B-concentrate on the purified water/A-concentrate mixture, sends a signal to logic implementer 20, which uses the signal to properly proportion the B-concentrate by controlling B-concentrate pump 44. The B conductivity signal is also temperature compensated via a reading from temperature sensor 48.

An expansion tank 50 deaerates the purified water prior to receiving the concentrates, removing bubbles from the water, which has been degassed in a chamber 51 via a degassing pump 53, located below expansion tank 50. A heater 52 controlled by logic implementer 20 heats the purified water for treatment to body temperature, e.g., 37° C. The fluid exiting conductivity cell 46 is therefore freshly prepared dialysis fluid, properly degassed and heated, and suitable for sending to dialyzer 102 for treatment. A fresh dialysis fluid pump 54, such as a gear pump, delivers the fresh dialysis fluid to dialyzer 102. Logic implementer 20 controls fresh dialysis fluid pump 54 to deliver fresh dialysis fluid to the dialyzer at a specified flowrate as described in more detail below.

A used dialysis fluid and drain line 56 via a used dialysis fluid pump 58 returns used dialysis fluid from the dialyzer to a drain 60. Logic implementer 20 controls used dialysis fluid pump 58 to pull used dialysis fluid from dialyzer 102 at a specified flowrate. An air separator 62 separates air from the used dialysis fluid in used dialysis fluid and drain line 56 to improve the accuracy of a downstream UF system 90 discussed below. A similar air separator 62 may be placed additionally upstream of UF system 90 in fresh dialysis fluid line 76. A further one or more air separator 62 may be placed alternatively or additionally downstream of a flow path insulator having an air isolation chamber of the present disclosure, to remove any air from fresh dialysis fluid in line 76 (and/or a substitution line) that becomes entrained due to the air isolation chamber. A pressure sensor 64 senses the pressure of used dialysis fluid within a used dialysis fluid and drain line 56 and sends a corresponding pressure signal to logic implementer 20.

Conductivity cell 66 measures the conductivity of used fluid flowing through the used dialysis fluid and drain line 56 and sends a signal to logic implementer 20. The conductivity signal of cell 66 is also temperature compensated via a reading from temperature sensor 68. A blood leak detector 70, such as an optical detector, looks for the presence of blood in drain line, e.g., to detect if a dialyzer membrane has a tear or leak. A heat exchanger 72 recoups heat from the used dialysis fluid exiting dialysis fluid circuit 30 to drain 60, preheating the purified water traveling towards heater 52 to recover and thereby conserve energy.

A fluid bypass line 74 allows fresh dialysis fluid to flow from fresh dialysis fluid line 76 to used dialysis fluid and drain line 56 without contacting dialyzer 102. A fresh dialysis fluid tube 78 extends from machine 12 and carries fresh dialysis fluid from fresh dialysis fluid line 76 to dialyzer 102. A used dialysis fluid tube 80 also extends from machine 12 and carries used dialysis fluid from dialyzer 102 to used dialysis fluid and used dialysis fluid and drain line 56.

Fresh dialysis fluid line also includes a conductivity sensor or cell 82 that senses the conductivity of fresh dialysis fluid leaving a UF system control unit 90 and sends a corresponding signal to logic implementer 20. The conductivity signal of cell 82 is likewise temperature compensated via a reading from temperature sensor 84.

An ultrafilter 86 further purifies the fresh dialysis fluid before being delivered via dialysis fluid line 76 and fresh dialysis fluid tube 78 to dialyzer 102. As discussed in more detail below, one or more ultrafilter 86 and 88 may be used to purify the fresh dialysis fluid to the point where it may be used as substitution fluid to perform pre- or post-dilution hemofiltration or hemodiafiltration.

UF system 90 monitors the flowrate of fresh dialysis fluid flowing to dialyzer 102 (and/or as substitution fluid flowing directly to the blood set (FIG. 2)) and used fluid flowing from the dialyzer. UF system 90 includes fresh and used flow sensors Q1*c* and Q2*c*, respectively, which send signals to logic implementer 20 indicative of the fresh and used dialysis fluid flowrate, respectively. Logic implementer 20 uses the signals to set used dialysis fluid pump 58 to pump faster than fresh dialysis fluid pump 54 by a predetermined amount to remove a prescribed amount of fluid from the patient through ultrafiltration ("UF") over the course of treatment. Fresh and used flow sensors Q1*p* and Q2*p* supervise the UF system 90 and alarm if discrepancies are detected.

System 10 provides plural valves 92 (collectively referring to valves 92*a* to 92*l*) under the control of logic implementer 20 to selectively control a prescribed treatment. In particular, valve 92*a* selectively opens and closes bypass line 74 to redirect the dialysis fluid flow away from dialyzer 102 (*i*) if any type of problem with the fresh dialysis fluid (e.g., wrong temperature or wrong conductivity) is detected or (ii) to allow disinfection fluid to flow from fresh dialysis fluid line 76 to used dialysis fluid and drain line 56. Valves 92*b* and 92*c* open and close the flow to dialyzer 102 through lines 78 and 80, respectively. Valve 92*d* selectively opens and closes used dialysis fluid and drain line 56 to drain 60. Valve 92*e* selectively opens and closes purified water line 32 to purified water source 22. Valves 92*f* and 92*g* control A- and B-concentrate flow, respectively. Valves 92*h* to 92*k* operate with UF system 90.

FIG. 1 further illustrates a substitution line 96 extending off of fresh dialysis fluid line 76. A valve 92*l* under control of logic implementer 20 selectively opens and closes substitution line 96. A substitution pump 94 under control of logic implementer 20 selectively pumps fresh dialysis fluid from ultrafilter 86 through a second ultrafilter 88 to produce substitution fluid, which is delivered via substitution line 96 (within machine 12) and a substitution tube 98 (external to machine 12) to arterial blood line 106 and/or venous blood line 108 instead of fresh dialysis fluid via line 76 (hemofiltration ("HF")) or in addition to fresh dialysis fluid via line 76 (for hemodiafiltration ("HDF")).

Referring now to FIG. 2, system 10 also includes a blood circuit or set 100 used with machine 12. In the illustrated embodiment, blood circuit or set 100 includes a dialyzer 102 having many hollow fiber semi-permeable membranes 104, which separate dialyzer 102 into a blood compartment and a dialysis fluid compartment. The dialysis fluid compartment during treatment is placed in fluid communication with an inlet from fresh dialysis fluid tube 78 and an outlet to used dialysis fluid tube 80. For HF and HDF, a separate substitution tube, in addition to fresh dialysis fluid tube 78, is placed during treatment in fluid communication with either the arterial line 106 or venous line 108. In HDF, dialysis fluid flows through tube 78 to dialyzer 102, while for HF, dialysis fluid flow through tube 78 is blocked.

An arterial pressure pod 114 is situated on arterial line 106 before blood pump 120 to ensure, for example, that no excessive negative pressure due to kinking or restriction is present in the arterial line. A system pressure pod 110 is placed between blood pump 120 and dialyzer 102, while venous line 108 includes venous a pressure pod 112. Pressure pods 110, 112 and 114 operate with blood pressure sensors (not illustrated) mounted on the machine housing. The arterial, venous and system pressure sensors send arterial, venous and system pressure signals, respectively, to logic implementer 20. Venous line 108 includes an air separation chamber or venous drip chamber 115, which removes air from the patient's blood before the blood is returned to patient 116.

Arterial line 106 of blood circuit or set 100 is operated on by blood pump 120, which is under the control of logic implementer 20 to pump blood at a desired flowrate. System 10 also provides multiple blood side electronic devices that send signals to and/or receive commands from logic implementer 20. For example, logic implementer 20 commands pinch clamps 122a and 122b to selectively open or close arterial line 106 and venous line 108, respectively. A blood volume sensor ("BVS") 124 is located along arterial line 106 upstream of blood pump 120. Air detector 126 looks for air in the venous blood line. Substitution tube 98 as illustrated may be coupled to arterial line 106 for pre-dilution HF or HDF and/or venous line 108 for post-dilution HF or HDF. Arterial line 106, venous line 108 and substitution line 98 are made of a suitably electrically insulating material, such as polyvinylchloride ("PVC") or silicone (e.g., pumping areas may be softer silicone). The blood lines are thick enough to reduce or eliminate a negligible level any voltages created due to a capacitive coupling.

The present disclosure includes one or multiple flow path insulators 150 placed in A-concentrate line 34, B-concentrate line 36, fresh dialysis fluid line 76, used dialysis fluid and drain line 56, arterial blood line 106 and/or venous blood line 108.

As used herein, flow path insulator 150 represents any of the insulating insulators 150a to 150e illustrated below in FIGS. 3 to 8. Flow path insulators 150 refers to plural ones of insulators 150a to 150e and/or to any combination of insulators 150a to 150e. To this end, concentrate lines 34, 36, fresh dialysis fluid line 76, used dialysis fluid and drain line 56, arterial blood line 106 and/or venous blood line 108 may each have one or multiple ones of flow path insulators 150. Flow path insulators 155a to 155d introduced below in FIGS. 9A to 9D (referred to collectively as flow path insulators 155) are flow path insulators (such as insulators 150) operated in combination with an air isolation chamber 200.

FIGS. 1 and 2 illustrate that any flow path insulator 150 may be located in any one or more of: (i) A-concentrate line 34, e.g., upstream of A-concentrate pump 38, (ii) B-concentrate line 36, e.g., upstream of B-concentrate pump 44, (iii) fresh dialysis fluid line 76, e.g., within machine 12 between a final downstream flow component (valve 92b) and dialyzer 102, (iv) used dialysis fluid and drain line 56, e.g., within machine 12 between a first upstream flow component (valve 92c and dialyzer 102, (v) used dialysis fluid and drain line 56, e.g., within machine 12 between a final downstream flow component (valve 92d) and drain 60, (vi) in arterial line 106, e.g., close to blood pump 120 and/or (vii) in venous line 108, e.g., in addition to venous drip chamber 115. Alternatively or additionally, any flow path insulator 150 may be used in place of (serving additionally the function of) air separator 62 in used dialysis fluid and drain line 56. Further alternatively or additionally, any flow path insulator 150 described herein may be placed in a portion of used dialysis fluid and drain line 56 located external to the housing of machine 12 as described below in connection with FIGS. 12A and 12B. Still further alternatively or additionally, the flow path insulators 150 may be used with concentrate coming from A-source 24, B-source 26 or from a central delivery system.

As discussed above, flow path insulators 150 may be placed inside machine 12 in A-concentrate line 34 and/or B-concentrate line 36. Such internal concentrate insulators are particularly useful with centralized concentrate systems (but are not limited to centralized concentrate), in which the concentrates come from a wall or large source rather than a container. When containers, such as sources 24 and 26, of concentrate are provided, the isolation is in one embodiment provided at the container itself, e.g., by ensuring that source 24, 26 is not in contact with a housing of machine 12 and/or is held off of the floor to prevent fault currents due to a capacitive coupling from being propagated from to and/or from the sources.

Figure 12A:
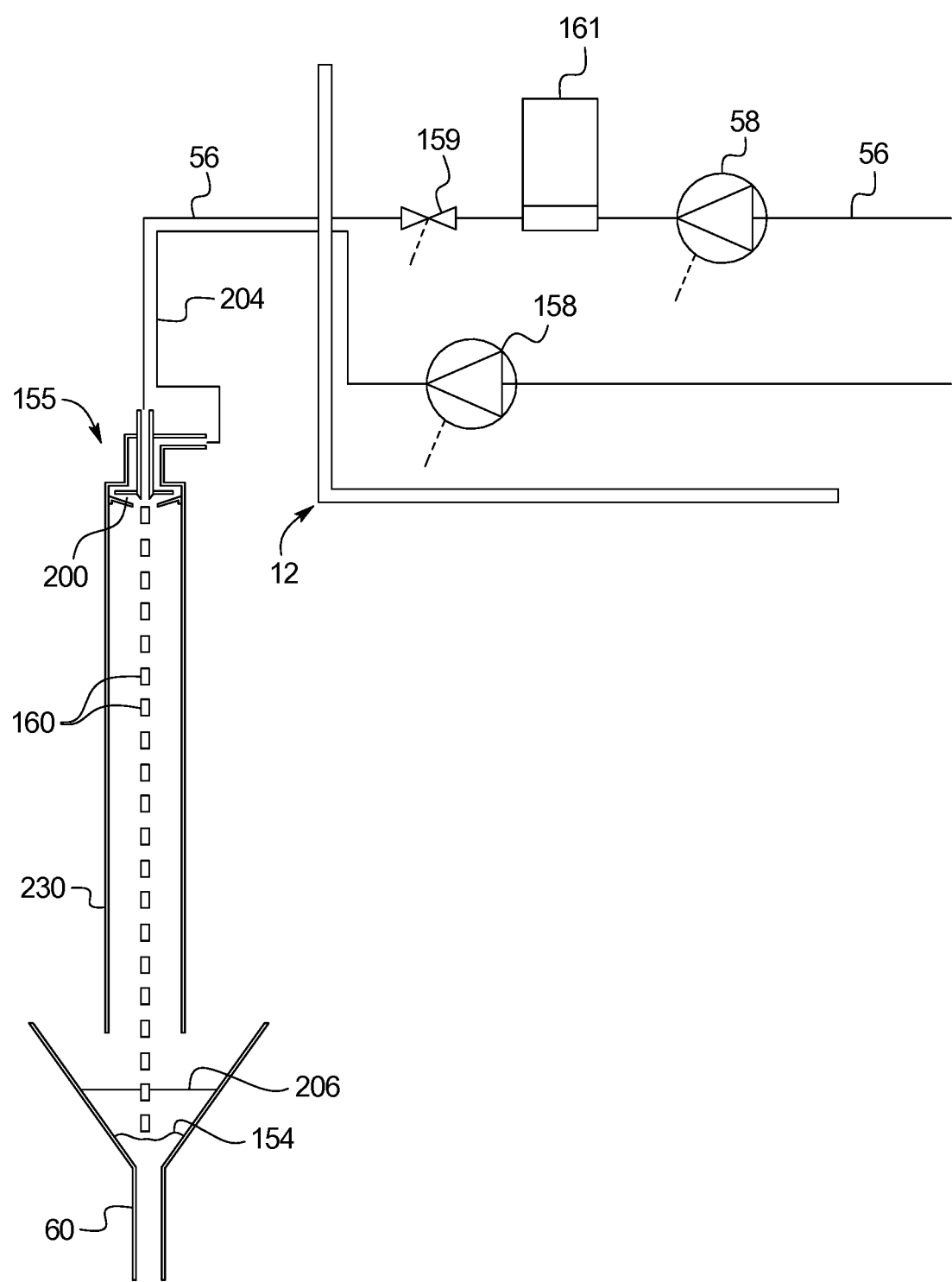
FIGS. 12A and 12B are flow schematic illustrating multiple flow path insulators of the present disclosure positioned and operating outside of the housing of a renal failure therapy machine.
Figure 12B:
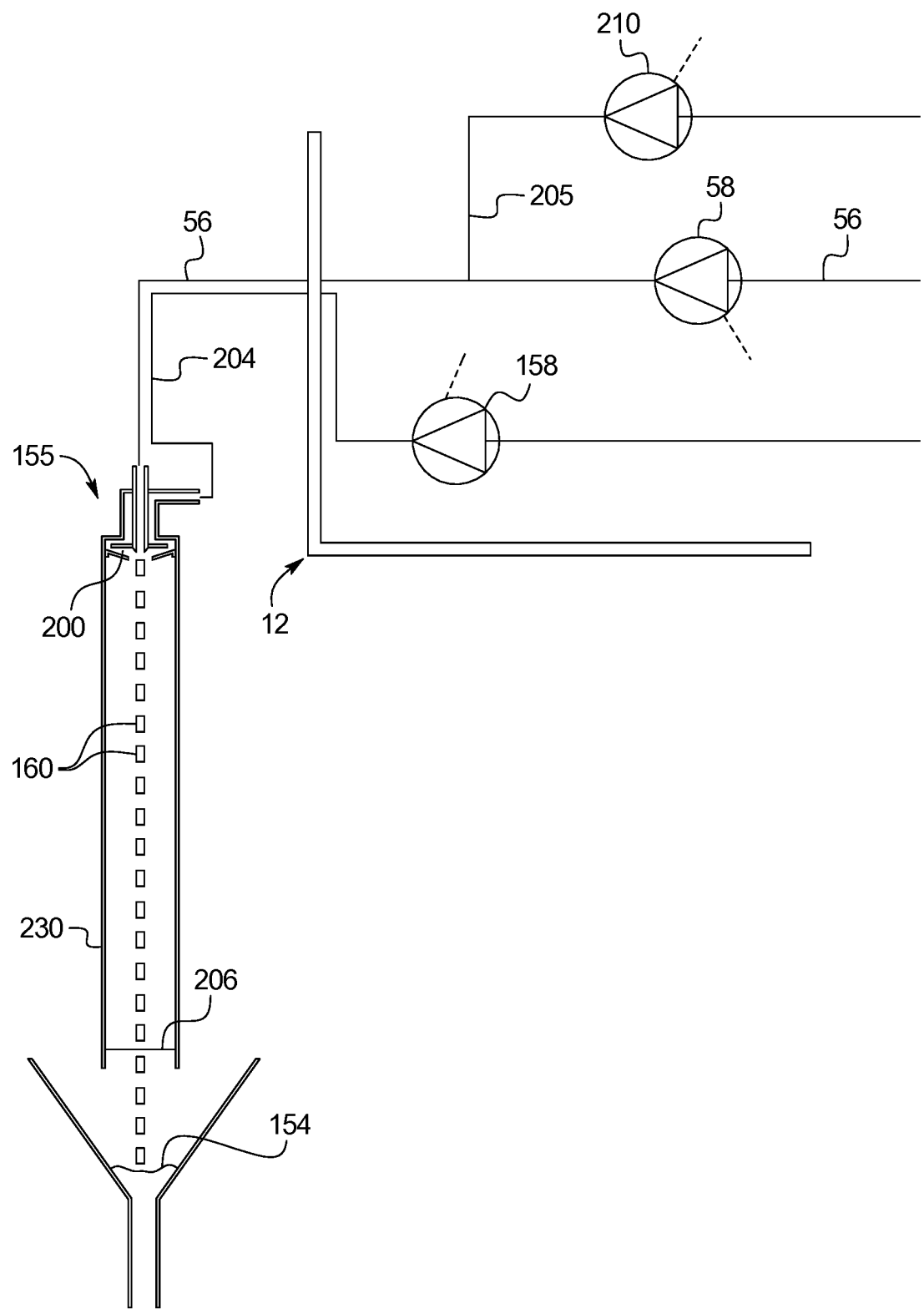

Referring now to FIG. 1B, in various embodiments, system 10 includes a single or multiple flow path insulator(s) 150 and/or 155 located at the end of the flow of machine 12, e.g., at the end of used dialysis fluid and drain line 56 in FIG. 1B, and/or outside of machine 12 as illustrated in FIGS. 12A and 12B. System 10 of FIG. 1B corresponds to the segmented line of electrical insulation defense A-A illustrated in FIG. 1A. Line of defense A-A uses flow path insulator(s) 150/155 located at the end of drain line and the protections discussed herein for A-concentrate container 24 and B-concentrate container 26. Here, all fluid flow components to the right of line of defense A-A (as indicated by the arrows), including virtually the entire dialysis fluid circuit 30, dialyzer 102 and blood flow in set 100, are made to be electrically floating. Flow path insulator 150/155 located at the end of used dialysis fluid and drain line 56 may therefore prevent any fault current from flowing through used dialysis fluid and drain line 56 to drain 60. Central concentrate lines should accordingly not be attached to machine 12, while concentrate containers 24 and 26 should be well isolated where they are located, e.g., be hung on machine instead of being placed on potentially wet concrete.

If purified water from source 22 is deionized, the water in line 32 is nonconductive. Realistically, however, a clinic may not provide sufficiently deionized water. It is therefore contemplated to place a flow path insulator 150/155 in water line 32, or place a conductivity cell in communication with the water flowing through water line 32 (e.g., upstream of expansion tank 50) to ensure that water from source 22 is sufficiently non-conductive. Alternatively, existing conductivity sensor 40 or 46 may be used to test the water prior to any concentrate from A-concentrate source 24 or B-concentrate source 26 being added to the water, e.g., at start-up during the filling of machine 12.

In an alternative embodiment, FIG. 1A illustrates that A-concentrate container 24 may have standoffs 25 located at the bottom of container 24, while B-concentrate container 26 may have standoffs 27 located at the bottom of container 26. Standoffs 25 and 27 both perform the same purpose, namely, they increase the dielectric gap between conductive liquid concentrate located within containers 24 and 26 and a potentially conductive moist or wet floor (e.g., concrete)

located within a dialysis clinic or center, to the point where any capacitive voltage created between the conductive concentrate and the moist or wet floor is either eliminated completely or is so small that it may be neglected. Standoffs 25 and 27 accordingly allow containers 24 and 26 to sit on the clinic floor if desired, while being electrically isolated from the floor.

Standoffs 25 and 27 may be molded or formed with the rest of containers 24 and 26, respectively, or be attached to the containers. Standoffs 25 and 27 are provided in a number suitable to hold containers 24 and 26 steady when resting on the clinic floor. The height of standoffs 25 to 27 is sufficient for the bottom of containers 24 and 26 to clear any moisture or pooling of water on the clinic floor, e.g., 12 mm. Alternatively, containers 24 and 26 may be hung from machine 12 to suspend the containers up from the clinic floor to reduce or eliminate the possibility of any capacitive voltage created between the conductive concentrate and the moist or wet floor.

To create the electrically floating dialysis fluid circuit 30, sensitive equipment, such as conductivity sensors 40, 46, 66 and 82, which are normally connected to earth ground, are not connected to earth ground. Likewise, the flow sensors Q1c, Q2c, Q1p, and Q2p of UF system 90 are not connected to protective earth. Indeed, nowhere is electrically floating dialysis fluid circuit 30 or the floating blood set 100 connected to protective earth ground (except in limited testing situations described below). Thus, dialysis fluid circuit 30 and the floating blood set 100 with respect to machine 12 are said to be electrically floating.

The sensitive equipment, however, is in the prior art connected to earth ground for a reason, namely, if not properly grounded, stray current from outside or inside the machine or a faulty component may cause the conductivity and flow sensors to read or output improperly. To combat this problem without connecting the sensors to earth ground, the sensors of the present disclosure are provided with electrical bypass lines 250 as illustrated in FIG. 1B. Bypass lines 250 electrically bypass the sensing equipment, from a point upstream of the sensors to a point downstream of the sensors, so that fault currents conduct from upstream to downstream of each sensor, or vice versa, through electrical bypasses 250 and not the sensing equipment. In doing so, bypass lines 250 electrically contact, or are otherwise in electrical communication with, fluid upstream of the sensors and fluid downstream of the sensors, creating a short circuit around the sensors. The short circuit causes stray currents to bypass the sensors, so that the stray currents do not affect the operation of the sensors.

Additionally, the sensors and any other flow component conductively touching liquid in the dialysis fluid circuit 30 and the blood set 100 is electrically insulated from the remainder of machine 12 via mechanical insulation. Mechanical insulation refers to the use of a non-conductive material, e.g., plastic, rubber, ceramic, and combinations thereof, placed between the fluid contacting component and the machine. The result may be an insulating pad located between the component and the machine chassis or other machine fixture to which the component is mounted.

Besides, the "mechanical" electrical insulation, to make the dialysis fluid circuit 30 and the blood set 100 floating, electrical power wires and electrical signal wires that conduct signals away from the sensor probes or other structures that contact the blood, dialysis fluid, or concentrate, for example, need to be electrically isolated from the circuitry and computational devices that read and analyze the sensor signals, e.g., printed circuit boards, processing, memory (discussed above as logic implementer 20). To do so, each power and signal wire stemming from a sensor is in one embodiment isolated via a transformer or optically isolated from a power or signal wire, respectively, that then extends from the optical isolator to logic implementer 20 or power source. The transformer has separate power coils. The optical signal isolator passes along the information carried by the sensor signal wiring, while creating a physical break in the signal lines. The physical breaks prevent (i) stray currents from machine 12 from entering the floating fluid pathway via the sensor power or signal lines and (ii) stray currents within floating fluid pathway from exiting out to machine 12 and its other components via the sensor power or signal lines.

So to make the dialysis fluid circuit 30 and the blood set 100 electrically floating, four features may be ensured: (i) no connection from a conductive fluid path to earth ground is made within machine 12 or the blood lines, (ii) sensitive equipment that touches conductive water, concentrate, dialysis fluid and/or blood in dialysis fluid circuit 30 and blood in blood set 100 is electrically bypassed, (iii) components that contact liquid are "mechanically" electrically insulated when mounted, and (iv) signal wires from logic implementer 20 are electrically isolated.

In a second embodiment, as illustrated by electrical insulation line of defense B-B in FIG. 1A, system 10 includes two flow path insulators 150 close to the fresh dialysis fluid valve 92b and used dialysis fluid valve 92c, and perhaps a third flow path insulator 150 located in substitution line 96 if substitution fluid is to be used for HDF. Here, all fluid components to the right of electrical insulation line of defense B-B need to be electrically floating, however, the majority of dialysis circuit to the left of the dialysis fluid circuit 30 does not need to be electrically floating. It is primarily blood set 100 in FIG. 2 that needs to be electrically floating for electrical insulation line of defense B-B. But blood set 100 is generally already electrically floating because it is not connected to earth ground and does not typically operate with invasive sensing equipment having conductive probes that contact blood. But if blood set 100 does employ blood side conductivity sensing, for example, then the sensor should be electrically bypassed via a bypass 250 discussed above and be isolated from earth ground as discussed herein.

As illustrated in FIG. 1A, an air separator 63 is placed downstream of the flow path insulator 150 located in fresh dialysis fluid line 76. If flow path insulator 150 in dialysis fluid line 76 employs the air isolation chamber 200 discussed below, and air becomes entrained in the fresh dialysis fluid thereby, air separator 63 may remove such air before reaching dialyzer 102. It should also be appreciated, however, that wetted membranes of dialyzer 102 provide an air barrier, such that air may not pass from the dialysis fluid side of dialyzer 102 to its blood side. It is nevertheless desirable to keep dialysis fluid circuit 30 free of air as much as possible because certain instruments, such as components of UF system 90, may be effected by air in the dialysis fluid.

An additional air separator 63 may be placed downstream of a flow path insulator 150 located in substitution line 96 for HDF. Here again, if flow path insulator 150 in substitution line 96 employs the air isolation chamber 200 discussed below, and air becomes entrained in the substitution fluid, additional air separator 63 may remove such air before reaching blood set 100.

In a third embodiment, as illustrated by electrical insulation line of defense C-C in FIG. 2, two flow path insulators 150 are provided instead in blood set 100. Here, arterial line 106 upstream of arterial flow path insulator 150 and venous line 108 downstream of venous flow path insulator 150 with respect to electrical insulation line of defense C-C need to be electrically floating, which they are naturally in most instances. Flow path insulators 150 in blood set 100 may be any of insulators 150a to 150e or any of flow path insulators 155a to 155d discussed below. Especially for home use, it is contemplated to provide one or more blood flow path insulator 150 when logic implementer 20 runs a single needle blood modality. Here, only one blood line 106 or 108 (FIG. 2) runs to patient 116, and flow path insulator 150 is located in the single blood line.

Figure 3:
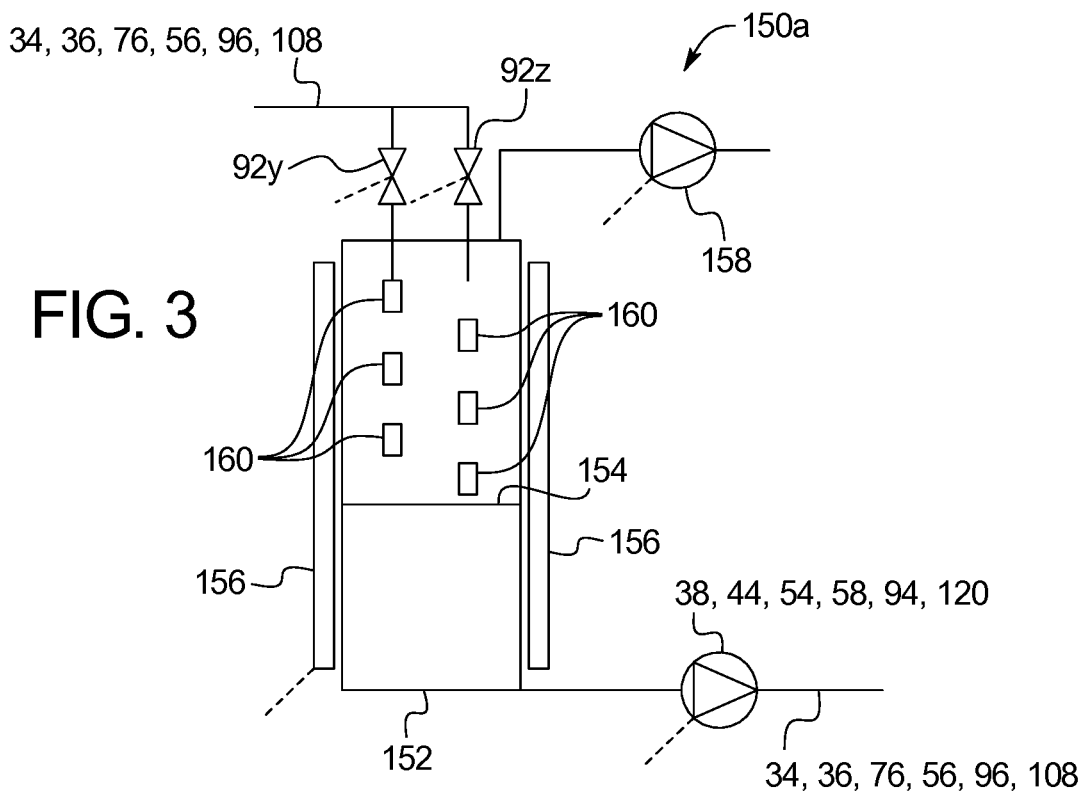
FIG. 3 is a sectioned elevation view of one embodiment of a flow path insulator of the present disclosure, which uses sequenced valves to create liquid segments or drops.

Referring now to FIG. 3, flow path insulator 150a illustrates a first insulator embodiment. Flow path insulator 150a includes a liquid container 152. Liquid container 152 in any of the insulator embodiments described herein may be made of any type of medically safe and electrically insulating plastic, ceramic, or glass. Liquid container 152 holds whatever liquid flows in along line 34, 36, 76, 56, 96 or 108, e.g., A-concentrate, B-concentrate, fresh dialysis fluid, used dialysis fluid, substitution fluid or blood. It should be appreciated that concentrate line 34 or 36 may convey concentrate from source 24 or 26, respectively, or concentrate from a central delivery system. The liquid forms a liquid/air interface 154 within container 152. Liquid/air interface 154 is monitored by a liquid level sensor 156, which outputs a signal indicative of the location of liquid/air interface 154 to logic implementer 20. Liquid level sensor 156 may be of any type known to those of skill, including optical, inductive, capacitive, and the like, which may be electrically floating. Logic implementer 20 uses the signal from liquid level sensor 156 to operate air pump 158, for example, to maintain liquid/air interface 154 at a desired level. Air pump 158 may be oriented to pull air out of container 152 as illustrated or to alternatively push air into container 152.

Flow path insulator 150a provides a plurality of control valves, here illustrated as two control valves 92y and 92z, under control of logic implementer 20. Valves 92y and 92z may be replaced alternatively with a single three-way valve. One, three or more control valves may be provided alternatively. Control valves 92y and 92z feed in parallel off of insulator inlet line 34, 36, 76, 56, 96 or 108 into the top of container 152. Logic implementer 20 for flow path insulator 150a controls (i) liquid/air interface 154 as described above so that a resulting insulation air gap within container 152 is sufficiently large and (ii) the opening and closing of each of control valves 92y and 92z, so that separate liquid segments or drops 160 are spaced apart from one another. Logic implementer 20 controls (i) and (ii) so that the length or diameter of the liquid segments is shorter than the insulation air gap to ensure that electrical continuity within flow path insulator 150a is interrupted or broken. In this manner, flow path insulator 150a prevents current flow within the corresponding flow path of machine 12 of system 10 due to a fault current generated from inside or outside of the machine.

One three-way valve or two or more control valves 92y and 92z help to maintain a desired flowrate through line 34, 36, 76, 56, 96 or 108. In an embodiment, the outlets of two or more control valves 92y and 92z are spaced apart enough so that their respective liquid segments or drops 160 do not comingle.

Figure 4:
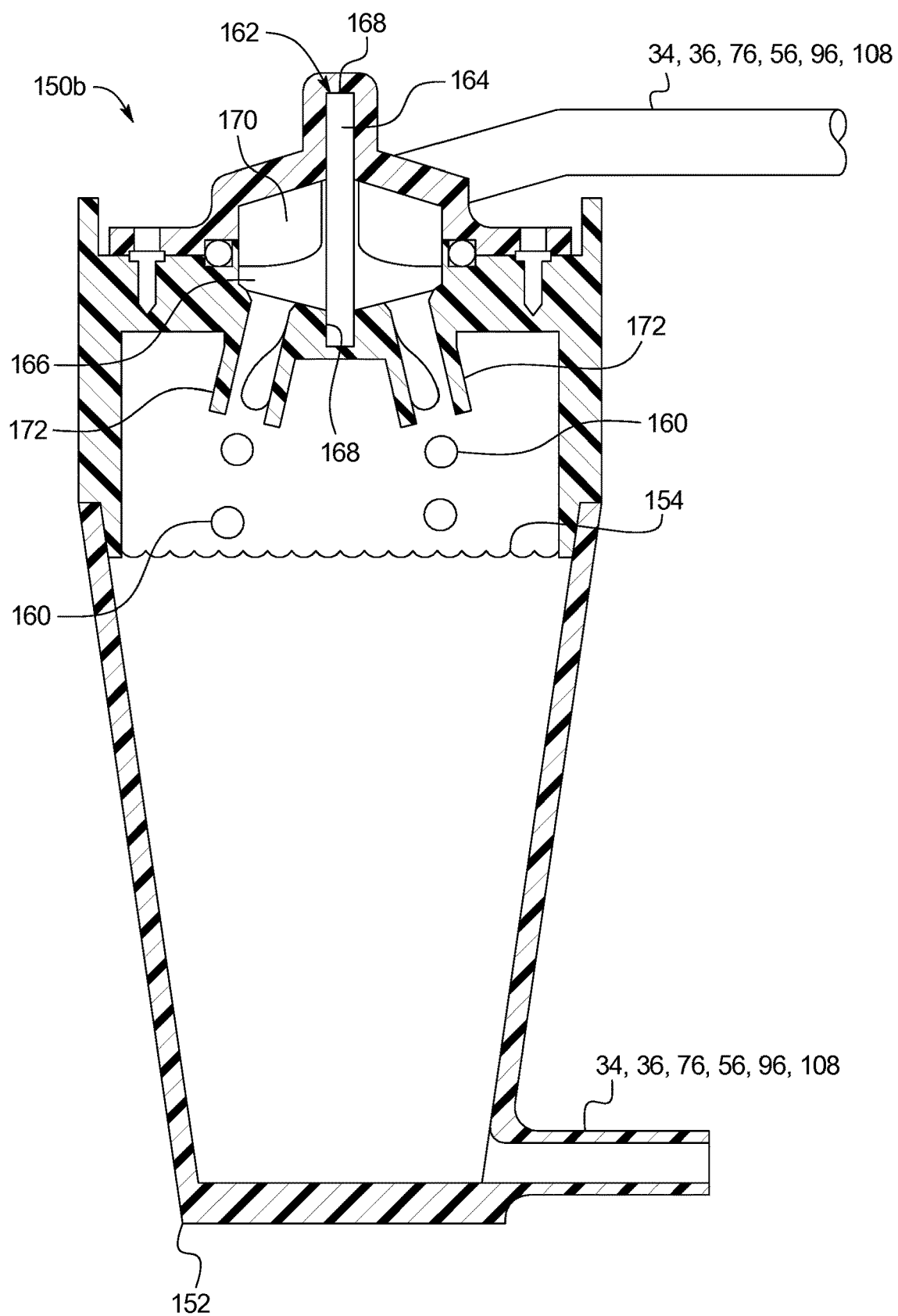
FIG. 4 is a sectioned elevation view of another embodiment of a flow path insulator of the present disclosure, which uses a turbine wheel to create liquid segments or drops.

Referring now to FIG. 4, flow path insulator 150b illustrates another insulator embodiment. Flow path insulator 150b also includes a liquid container 152, which (along with any of the insulator embodiments described herein) may have a tapered, non-tapered or oppositely tapered shape as the one illustrated in FIG. 4. Liquid container 152 again holds whichever liquid flows in along line 34, 36, 76, 56, 96 or 108, e.g., A-concentrate, B-concentrate, fresh dialysis fluid, used dialysis fluid, substitution fluid or blood. It should be appreciated that concentrate line 34 or 36 may convey concentrate from source 24 or 26, respectively, or concentrate from a central delivery system. The liquid again forms a liquid/air interface 154 within container 152. Although not illustrated in FIG. 4 (but described above in connection with insulator 150a of FIG. 3), flow path insulator 150b may operate with liquid level sensor 156, air pump 158 and logic implementer 20 as described above to control liquid/air interface 154 at a desired level.

Flow path insulator 150b includes a turbine wheel 162 located at the top of container 152. Turbine wheel 162 includes a shaft 164 having multiple blades 166 that spin horizontally within the top of container 152. Shaft 164 is held at either end in bearing relationship with upper and lower blind bores 168 formed in the top of container 152. Inlet line 34, 36, 76, 56, 96 or 108 introduces liquid into a chamber 170 formed above spinning blades 166. One or more outlet port 172 is provided in the top of container 152 to distribute liquid segments 160, formed at the outlet of port 172, into container 152. Multiple outlet ports 172 may be provided to obtain a desired liquid flowrate through flow path insulator 150b.

Turbine wheel 162 may either be driven by the force of fluid flow, creating a horizontal driving force, or be driven alternatively by a motor or via magnetic field generation. Turbine blade 166 may be formed with holes or openings, which when rotated, open and close outlet ports 172 in a desired manner.

Figure 5:
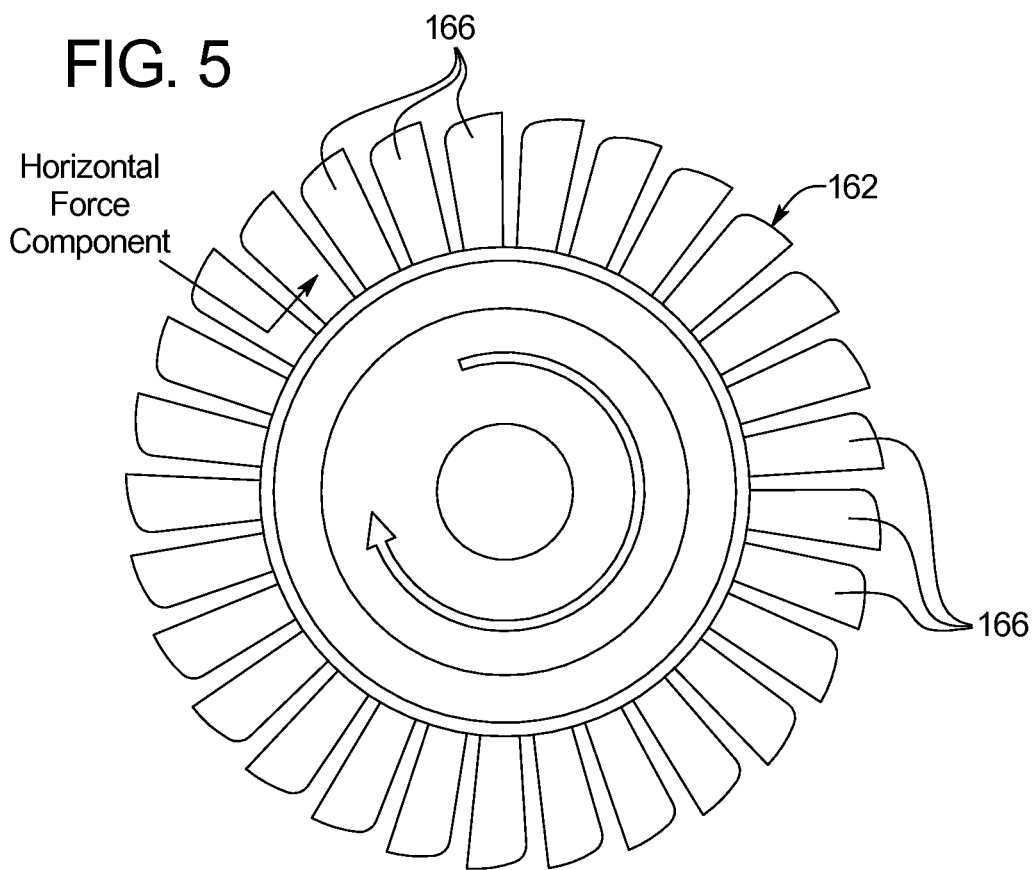
FIG. 5 is a top view of one embodiment of a turbine wheel used with the flow path insulator of FIG. 4.

Referring now to FIG. 5, an embodiment for blades 166 of turbine wheel 162 is illustrated. Shaft 164 and blades 166 of turbine wheel 162 may be made of any type of medically safe and electrically insulating plastic, ceramic, or glass. Blades 166 in the illustrated embodiment are angled so that there is a horizontal force vector component imparted to the blades (as indicated by the straight line arrow) when the liquid from inlet line 34, 36, 76, 56, 96 or 108 impinges the tops of the blades. The horizontal force vector component spins blades 166 and shaft 164 horizontally within liquid container 152, so that blades 166 as they spin alternatingly cover and open outlet ports 172, creating separate liquid segments or drops 160 that are distributed through outlet ports 172 and into the insulation air gap located above liquid/air interface 154. In the illustrated embodiment, the orientation of the angle of blades 166 causes a clockwise rotation, as indicated by the circular arrow in FIG. 5.

While the spinning of turbine wheel 162 creates liquid segments or drops 160, logic implementer 20 may use feedback from sensor 156 to control the insulation air gap within container 152 via the location of liquid/air interface 154, so that the length or diameter of the liquid segments 160 is shorter than the insulation air gap to ensure that electrical continuity within flow path insulator 150b is interrupted or broken. In this manner, flow path insulator 150b prevents a fault current generated via a fault condition from conducting within system 10.

In an alternative embodiment, it is possible to achieve properly spaced and sized liquid segments 160 with turbine wheel 162 and its blades 166 alone, wherein open outlet ports 172 are not needed, and wherein the insulation air gap begins immediately below blades 166.

Figure 6:
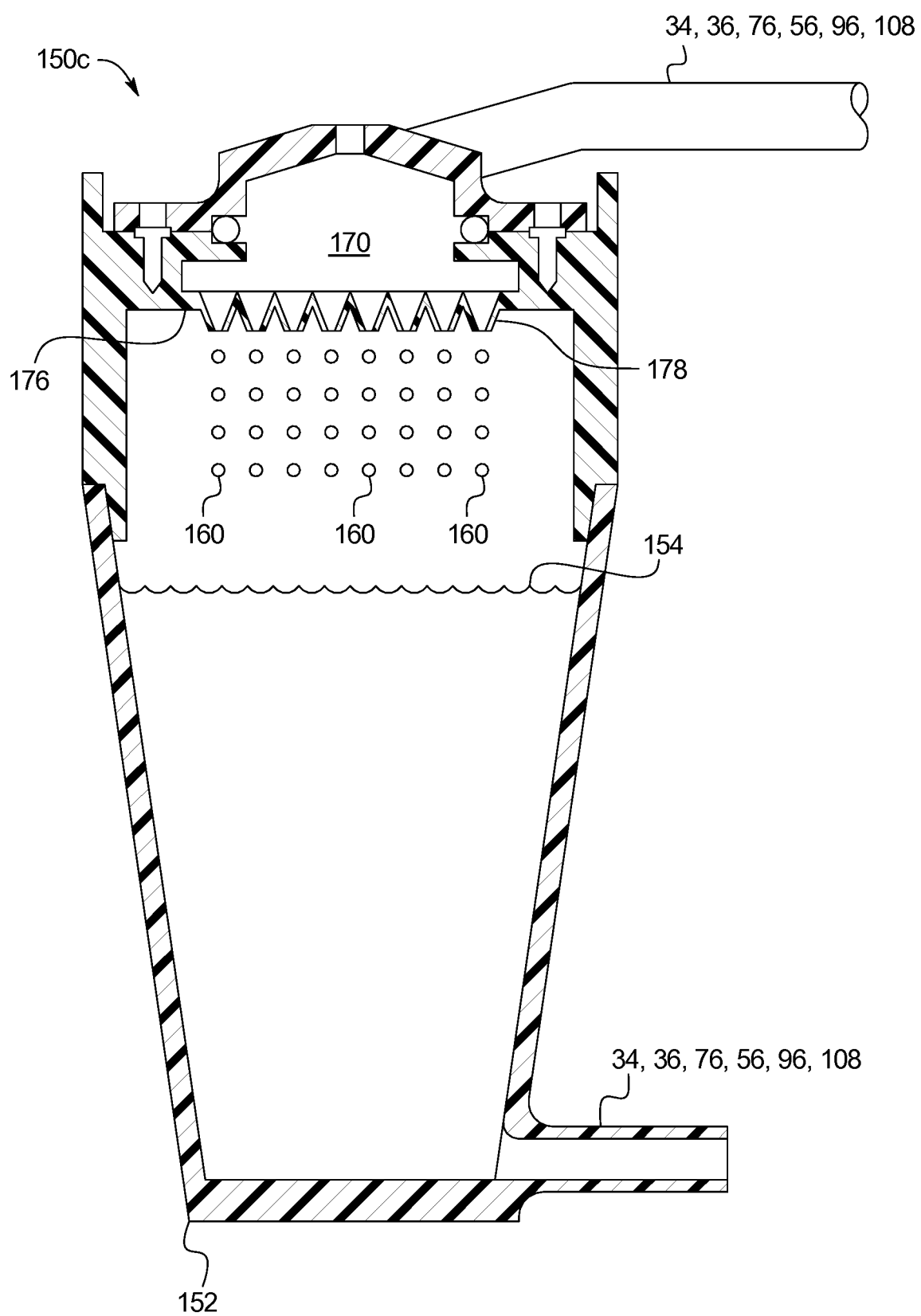
FIG. 6 is a sectioned elevation view of a further embodiment of a flow path insulator of the present disclosure, which uses a shower type manifold to create liquid segments or drops.

Referring now to FIG. 6, flow path insulator 150c illustrates a further insulator embodiment. Flow path insulator 150c also includes a liquid container 152, which may have a tapered, non-tapered or oppositely tapered shape as the one illustrated in FIG. 6. Liquid container 152 again holds whichever liquid flows in along line 34, 36, 76, 56, 96 or 108, e.g., A-concentrate, B-concentrate, fresh dialysis fluid, used dialysis fluid, substitution fluid or blood. It should be appreciated that concentrate line 34 or 36 may convey concentrate from source 24 or 26, respectively, or concentrate from a central delivery system. The liquid again forms a liquid/air interface 154 within container 152. Although not illustrated in FIG. 6, flow path insulator 150c may operate with liquid level sensor 156, air pump 158 and logic implementer 20 as described above to control liquid/air interface 154 at a desired level.

Flow path insulator 150c includes a manifold plate 176 located as a bottom wall at the top of liquid container 152. Manifold plate 176 defines a plurality of nozzles or taps 178, which are narrow enough to cause liquid entering a chamber 170, defined in part by manifold plate 176, to be nozzled into separate liquid segments or drops 160. Manifold plate 176 may have a flat shape as illustrated or be slightly bowed. Nozzles 178 may be projected at an angle relative to vertical, so that the resulting liquid segments or drops 160 extend radially away from each other to dissuade comingling.

While the shower effect of manifold plate 176 creates liquid segments or drops 160, logic implementer 20 may use level sensor 156 to control the insulation air gap within container 152 via the location of liquid/air interface 154, so that the length or diameter of the liquid segments 160 is shorter than the insulation air gap to ensure that electrical continuity within flow path insulator 150c is interrupted or broken. In this manner, flow path insulator 150c prevents a fault current generated via a fault condition from conducting within system 10.

In a further alternative embodiment, turbine wheel 162 of FIGS. 4 and 5 is combined with manifold plate 176 and its shower apertures 178 to produce separate liquid segments or drops 160 within a single flow path insulator.

Figure 7:
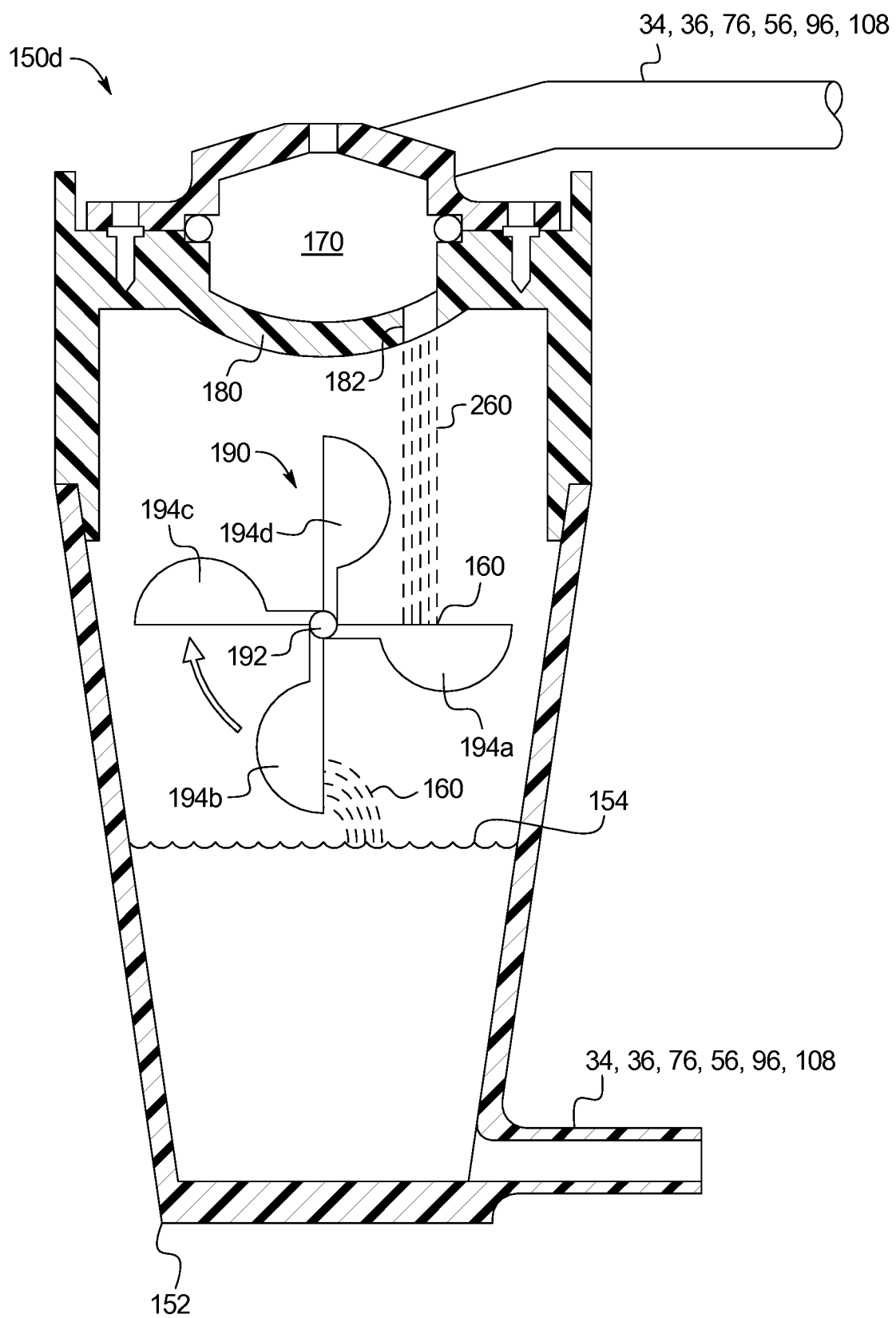
FIG. 7 is a sectioned elevation view of yet another embodiment of a flow path insulator of the present disclosure, which uses a paddle wheel type structure to create liquid segments or drops.

Referring now to FIG. 7, flow path insulator 150d illustrates yet another insulator embodiment. Flow path insulator 150d also includes a liquid container 152, which may have a tapered shape as illustrated in FIG. 7, a non-tapered shape, or an oppositely tapered shape from that of FIG. 7. Liquid container 152 again holds whichever liquid flows in along line 34, 36, 76, 56, 96 or 108, e.g., A-concentrate, B-concentrate, fresh dialysis fluid, used dialysis fluid, substitution fluid or blood. It should be appreciated that concentrate line 34 or 36 may convey concentrate from source 24 or 26, respectively, or concentrate from a central delivery system. The liquid again forms a liquid/air interface 154 within container 152. Although not illustrated in FIG. 7, flow path insulator 150d may operate with liquid level sensor 156, air pump 158 and logic implementer 20 as described above to control liquid/air interface 154 at a desired level.

Flow path insulator 150d includes a plate 180 located as a bottom wall at the top of liquid container 152. Plate 180 defines a single larger aperture 182, which allows for a steady stream of liquid 260 to flow from chamber 170, such that a desired flowrate through flow path insulator 150d may be obtained. Plate 180 may have a bowed or spherical shape as illustrated, to better hold the pressure of the liquid within chamber 170. Aperture 182 is nevertheless vertically disposed in the illustrated embodiment.

Flow path insulator 150d includes a paddle wheel 190, which rotates clockwise in the illustrated embodiment about a horizontally disposed shaft or axis 192. Paddle wheel 190 may be formed from any medically safe plastic or metal. Paddle wheel 190 includes a plurality of paddles, cups or troughs (referred to herein collectively as receptacles) 194a to 194d, which are filled individually via stream 260. While four receptacles 194a to 194d are illustrated, any three or more receptacles may be provided instead if driven by liquid, or any two or more receptacles may be provided if driven externally, e.g., motor driven. In the illustrated embodiment, as receptacle 194a fills with liquid and receptacle 194b empties liquid onto liquid/air interface 154, paddle wheel 190 turns to introduce a new, empty receptacle 194d to stream 260. The continuous rotation of paddle wheel 190 separates stream 260 into discrete and separate segments 160 via receptacles 194a to 194d, which are carried above liquid/air interface 154 to break electrical continuity within stream 260.

While paddle wheel 190 spins and breaks electrical continuity as described above, logic implementer 20 may use sensor 156 to control the insulation air gap within container 152 via the location of liquid/air interface 154, so that the liquid/air interface always resides below the lowest rotating receptacle 194a to 194d. In this manner, paddle wheel 190 may rotate freely to prevent current from flowing within a corresponding flow path of machine 12 due to a fault current generated inside or outside of the machine.

As with turbine wheel 162 of insulator 150b, paddle wheel 190 may be driven via the force of fluid stream 260 as discussed above, be driven electromechanically, and/or be slowed by a breaking mechanism or added mass. For example, logic implementer 20 may control an electrical motor (not illustrated) to spin axis or shaft 192 and receptacles 194a to 194d at a desired angular speed to achieve desired separate fluid segments 160.

Figure 8:
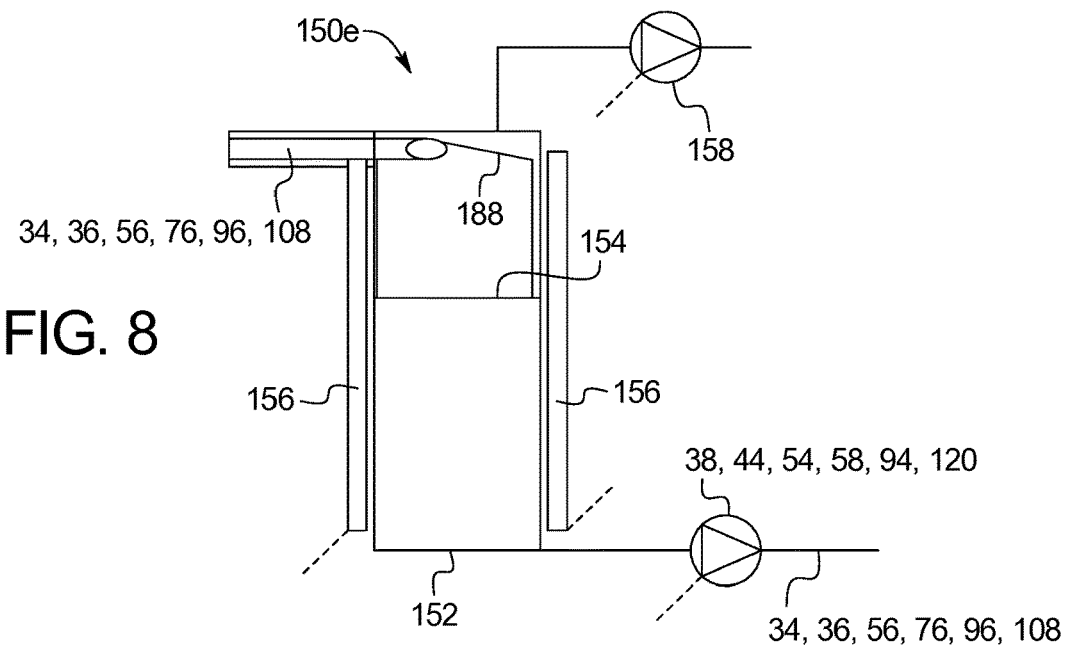
FIG. 8 is a sectioned elevation view of still another embodiment of a flow path insulator of the present disclosure, which uses tangential flow to create a high resistance film within the insulator.

Referring now to FIG. 8, flow path insulator 150e illustrates still a further insulator embodiment. Flow path insulator 150e also includes a liquid container 152, which may have a cylindrical shape as illustrated in FIG. 8, tapered shape as illustrated above, or other suitable non-cylindrical shape. Liquid container 152 again holds whichever liquid flows in along line 34, 36, 76, 56, 96 or 108, e.g., A-concentrate, B-concentrate, fresh dialysis fluid, used dialysis fluid, substitution fluid or blood. It should be appreciated that concentrate line 34 or 36 may convey concentrate from source 24 or 26, respectively, or concentrate from a central delivery system. The liquid again forms a liquid/air interface 154 within container 152. FIG. 8 illustrates that flow path insulator 150e may operate with liquid level sensor 156, air pump 158 and logic implementer 20 as described above to control liquid/air interface 154 at a desired level.

The inlet 34, 36, 76, 56, 96 or 108 into liquid container 152 is disposed horizontally, such that liquid is introduced sideways and tangential to an inner wall of container 152. The liquid spreads out along the inner wall of container 152, forming a thin film. The thin film migrates from the top of liquid container 152 into liquid/air interface 154. Top wall 188 of liquid container 152 as illustrated may angle downwardly as it extends away from the distal end of inlet 34, 36, 76, 56, 96 or 108 to help direct the thin film into a downwardly spiraling flow pattern. The thin thickness of the film ensures a very high electrical impedance within flow path insulator 150e, e.g., on the order of ten megaohms or greater. The very high impedance limits a fault current at flow path insulator 150e and thus through system 10 to a very low, harmless value. It is also contemplated to make the distance from where the film starts (at or beneath inlet line 34, 36, 76, 56, 96 or 108) down to the liquid/air interface 154 a minimum distance to ensure a high enough electrical impedance.

Figure 9A:
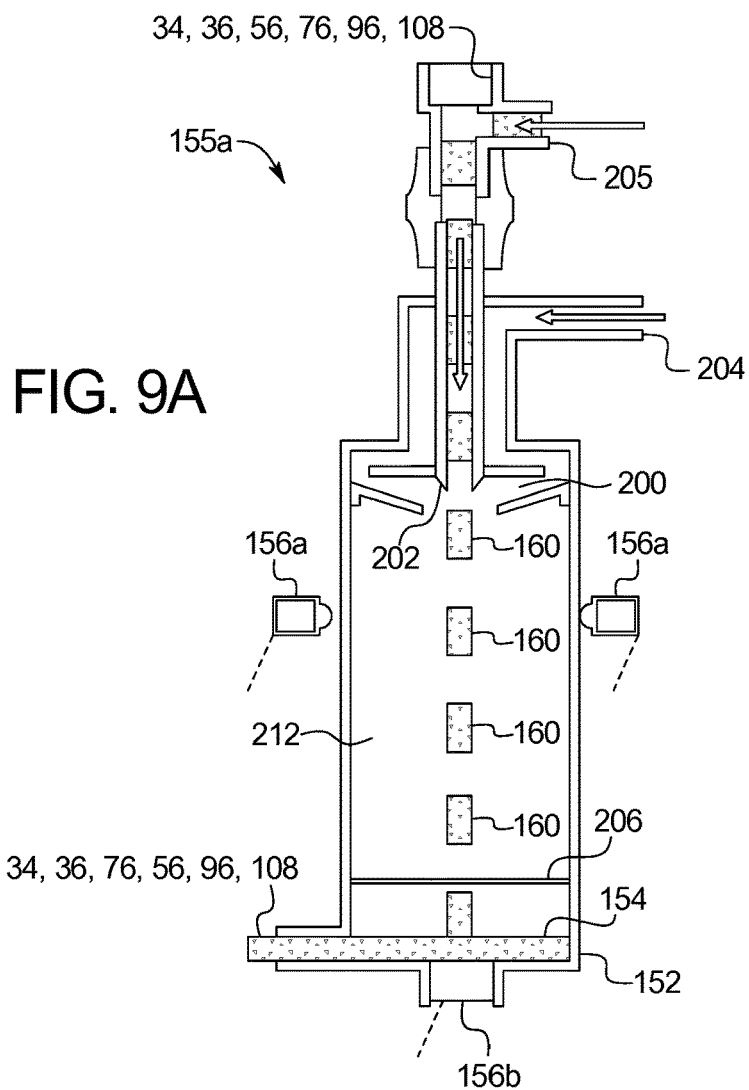
FIG. 9A is a sectioned elevation view of yet a further embodiment of a flow path insulator of the present disclosure, which provides one example for creating liquid segments in combination with the use of an air isolation chamber to help maintain an environment conducive to forming and maintaining the segments.

Referring now to FIGS. 9A to 12C, flow path insulators 155a to 155d (referred to collectively as flow path insulators 155) illustrate still a further insulator embodiment. Flow path insulators 155 also include a liquid container 152, which may have a cylindrical shape as illustrated in FIG. 9A and be made of any of the materials discussed herein. Liquid container 152 again holds whichever liquid flows in along line 34, 36, 76, 56, 96 or 108, e.g., A-concentrate, B-concentrate, fresh dialysis fluid, used dialysis fluid, substitution fluid or blood. It should be appreciated that concentrate line 34 or 36 may convey concentrate from source 24 or 26, respectively, or concentrate from a central delivery system. The liquid again forms a liquid/air interface 154 within container 152. FIG. 9A illustrates that flow path insulator 155a may operate with a side-mounted sensor 156a (e.g., optical) and/or a bottom-mounted sensor 156b (e.g., ultrasonic), an air pump 158 (not illustrated in FIG. 9A) and logic implementer 20 as described above to control liquid/air interface 154 at a desired level. Sensors 156a and 156b and logic implementer 20 are alone or together part of a testing apparatus of the present disclosure.

Flow path insulators 155 each include an air isolation chamber 200 located at the top of liquid container 152. That is, liquid container 152 includes two chambers, an upper chamber, which is the air isolation chamber 200, and a lower chamber 212, which is the chamber in which liquid/air interface 154 is maintained. Air isolation chamber 200 (the upper chamber) is controlled to ensure a clean surface. No concentrate, fresh or used dialysis fluid, substitution fluid or blood flows into air isolation chamber 200. Only fluid used during cleaning and disinfection may flow through air isolation chamber 200 in one embodiment. The surfaces of air isolation chamber 200 are kept dry during treatment to ensure that no current may sneak along the inner surfaces of the chamber. Lower chamber 212 will be wet during treatment with concentrate, fresh or used dialysis fluid, substitution fluid or blood. Lower chamber 212 will accept fluid segments 160 created above within air isolation chamber 200 via any of the flow path insulators discussed above. Dry air is pumped through upper air isolation chamber 200, keeping air isolation chamber 200 dry, and is exhausted out though lower chamber 212 in one embodiment, helping to reduce humidity in the lower chamber, and thus its overall conductivity.

In the illustrated embodiment, air isolation chamber 200 surrounds a distal nozzle end 202 of inlet line 34, 36, 76, 56, 96 or 108. Nozzle end 202 dispenses liquid segments or drops 160, e.g., via the sequencing one or more valve 92y and/or 92z, as discussed above in connection with flow path insulator 150a of FIG. 3. Air isolation chamber 200 may alternatively be used with and thereby protect (i) the multiple valved outlets of insulator 150a of FIG. 3, (ii) the outlet ports 172 of insulator 150b of FIG. 4 residing beneath turbine wheel 162 of FIGS. 4 and 5, (iii) manifold plate 176 and multiple nozzles 178 of insulator 150c of FIG. 6, and/or (iv) single larger aperture 182 of insulator 150d of FIG. 7. Thus, any of the structures of insulators 150a to 150d discussed above may be used with an air isolation chamber 200. Accordingly, when discussing flow path insulators 150a to 150d anywhere in this disclosure, it is to be understood that those insulators may or may not be operating with an air isolation chamber 200, as illustrated and described in connection with flow path insulator 155.

The inner surfaces of any liquid container 152 during treatment or over time may become wet and form a buildup of biological or salt deposits, which may create an undesired electrically conductive pathway between liquid/air interface 154 and nozzle end 202 (or the droplet producing ends of each of flow path insulators 150a to 150d), which may compromise the effectiveness of the flow path insulators. The biological and/or salt deposits will begin at liquid/air interface 154 and migrate or creep upwardly towards nozzle end 202 (or the other droplet producing ends). The salt and/or film may build on the walls and create a creeping film upon which electrical current may creep and devastate the isolation capacity of container 152. Providing air isolation chamber 200 with dry air, where no dialysis fluid or concentrate flows during treatment, secures the isolation integrity in air isolation chamber 200, prevents the film and/or salt build-up, and reduces or even eliminates creep currents along the inner walls of air isolation chamber 200. One interpretation of what constitutes dry air is that the air is dry enough to ensure that no condensation forms on the inside of the walls of container 152. Air within machine 12 will tend to be warmer than ambient due to the operating components of the machine, which helps prevent condensation. If needed, the air may be preheated, e.g., to 50'C or more.

As illustrated in FIG. 9A, air isolation chamber 200 receives pumped air via an air line 204. The pumped air is directed (may be pressurized) to all surfaces within air isolation chamber 200. The air is also pressed into lower chamber 212 (and eventually evacuated through the outlet pipe in the bottom of the chamber together with the dialysis fluid) to lower the humidity within chamber 212, thereby mitigating the possible formation of conductive biological or salty films and creep current along the walls in the lower chamber 212.

The continuous pumping of dry air into lower chamber 212 also tends to prevent electrical discharge and creep, which is also possible in the salty and humid air residing in lower chamber 212. The prevention of electrical discharge and creep in turn prevents leakage current between flow segments or drops 160.

FIG. 9A also illustrates that flow path insulators 155 (or any of the other flow path insulators 150a to 150e described herein) may each be provided with a splashguard 206. Splashguard 206 may be made of a medically safe rubber, such as silicone. Splashguard 206 may for example have one or more flaps and have a shape the same as or similar to the protective rubber guards found in sinks above garbage disposals. Splashguard 206 also helps to prevent the unwanted electrically conductive pathway from forming within liquid container 152. Although FIG. 9A illustrates splashguard 206 placed below sensor pair 156a, FIGS. 9C and 11 below illustrate an alternative embodiment in which splashguard is placed above sensor pair 156a.

FIG. 9A further illustrates that any flow path insulator 150, 155 may employ an optical sensor 156a and an ultrasonic sensor 156b in signal communication with logic implementer 20, for example, to monitor liquid segments or drops 160. Ultrasonic sensor 156b may be used as a backup sensor to optical sensor 156a and/or to sense independently for drops or segments 160, e.g., sending a pattern of ultrasonic output to logic implementer 20 indicative of, for example, proper drops 160, borderline drops 160, or no drops 160. Optical sensor 156a may include one or more camera or include an emitting and receiving optical pair, e.g., an infrared emitting and receiving pair. In any case, optical sensor 156a sensor sends a signal to logic implementer. The signal may for example be +5 VDC when a liquid segment or drop 160 is present and 0 VDC when a liquid segment or drop 160 is not present. Here, logic implementer 20 looks to make sure that a sufficient 0 VDC signal is observed between two liquid segments 160 being present signals at +5 VDC. System 10 may for example ensure that at least a 5 mm gap exists between liquid segments or drops 160. If so, logic implementer 20 allows treatment to continue. If not, logic implementer 20 causes system 10 to sound and/or display and audio, visual, or audiovisual alarm, which prompts the nurse to either shut down treatment or override the alarm if it is deemed that the threat to the patient is minimal even though insulator 155 (or alternatively any of flow path insulators 150*a* to 150*d* operating with air isolation chamber 200) may not be functioning properly.

FIG. 9A additionally illustrates one embodiment for creating drops or segments 160 in combination with the use of air isolation chamber 200. In the illustrated embodiment, a second air line 205 is provided. Here, a second air pump (discussed in more detail below with FIG. 10) is controlled by logic implementer 20 to provide pressurized bursts of air that interrupt water, blood, or dialysis fluid flow through line 34, 36, 76, 56, 96 or 108. The interruption causes the formation of segments or drops 160.

Figure 9B:
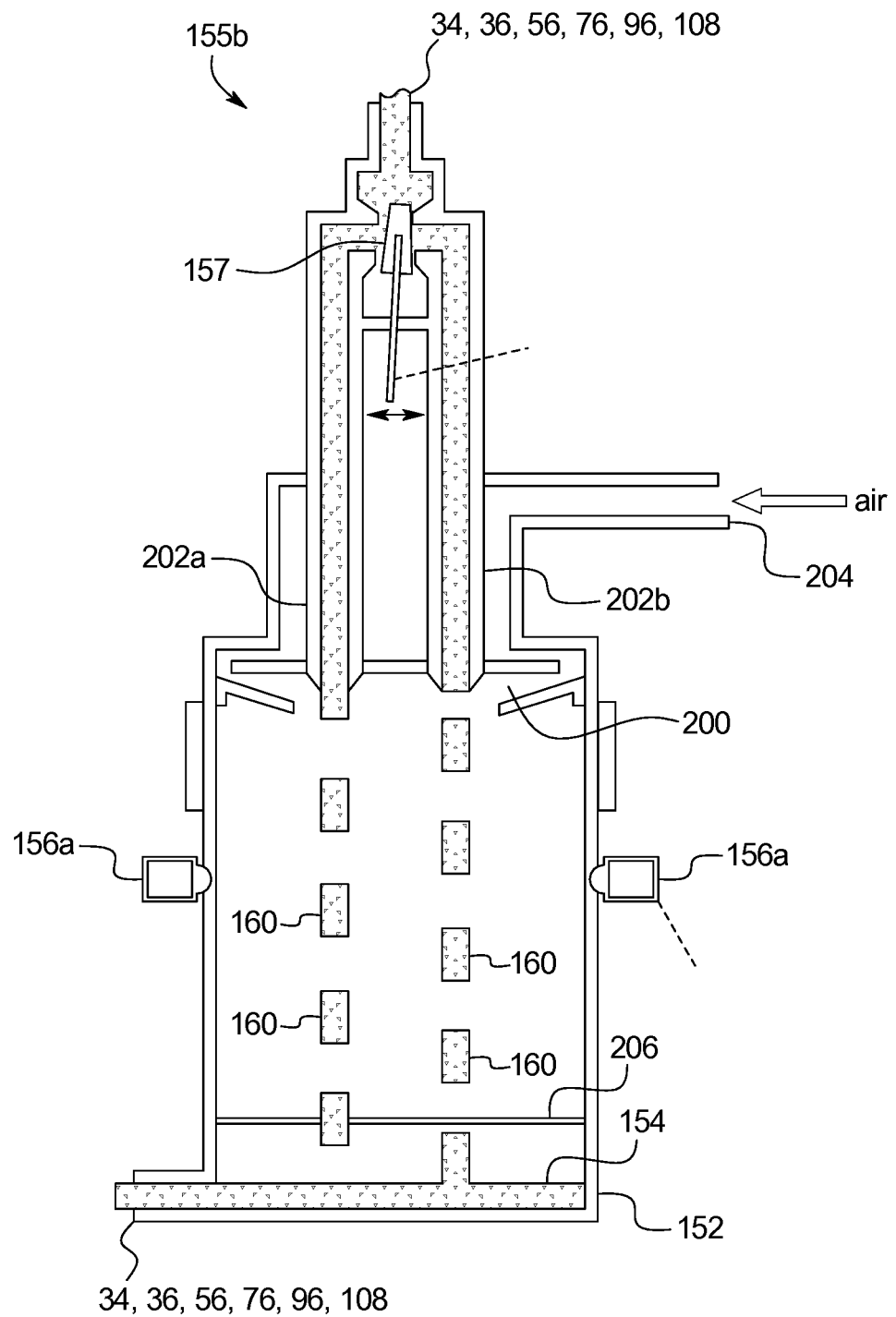
FIG. 9B is a sectioned elevation view of still a further embodiment of a flow path insulator of the present disclosure, which provides a second example for creating liquid segments in combination with the use of an air isolation chamber to help maintain an environment conducive to forming and maintaining the segments.

Flow path insulator 155*b* of FIG. 9B illustrates another embodiment for creating drops or segments 160 in combination with the operation of air isolation chamber 200. Flow path insulator 155*b* includes all of the structure, functionality and alternatives discussed herein for line 34, 36, 76, 56, 96 or 108, container 152, liquid/air interface 154, level sensors 156*a*/156*b*, air isolation chamber 200, and air inlet line 204. Flow path insulator 155*b* also includes a three-way valve 157 under control of logic implementer 20. Three-way valve 157 may be an electrically actuated solenoid valve, for example. Logic implementer 20 causes three-way valve 157 to toggle back and forth to split the water, blood, or dialysis fluid (i) into fluid segments 160 and (ii) into two separate flow pathways, exiting respectively at nozzle ends 202*a* and 202*b*. Air isolation chamber 200 surrounds fluid segments 160 exiting nozzle ends 202*a* and 202*b* so as to keep the spaces between segments 160 dry and non-conductive.

Figure 9C:
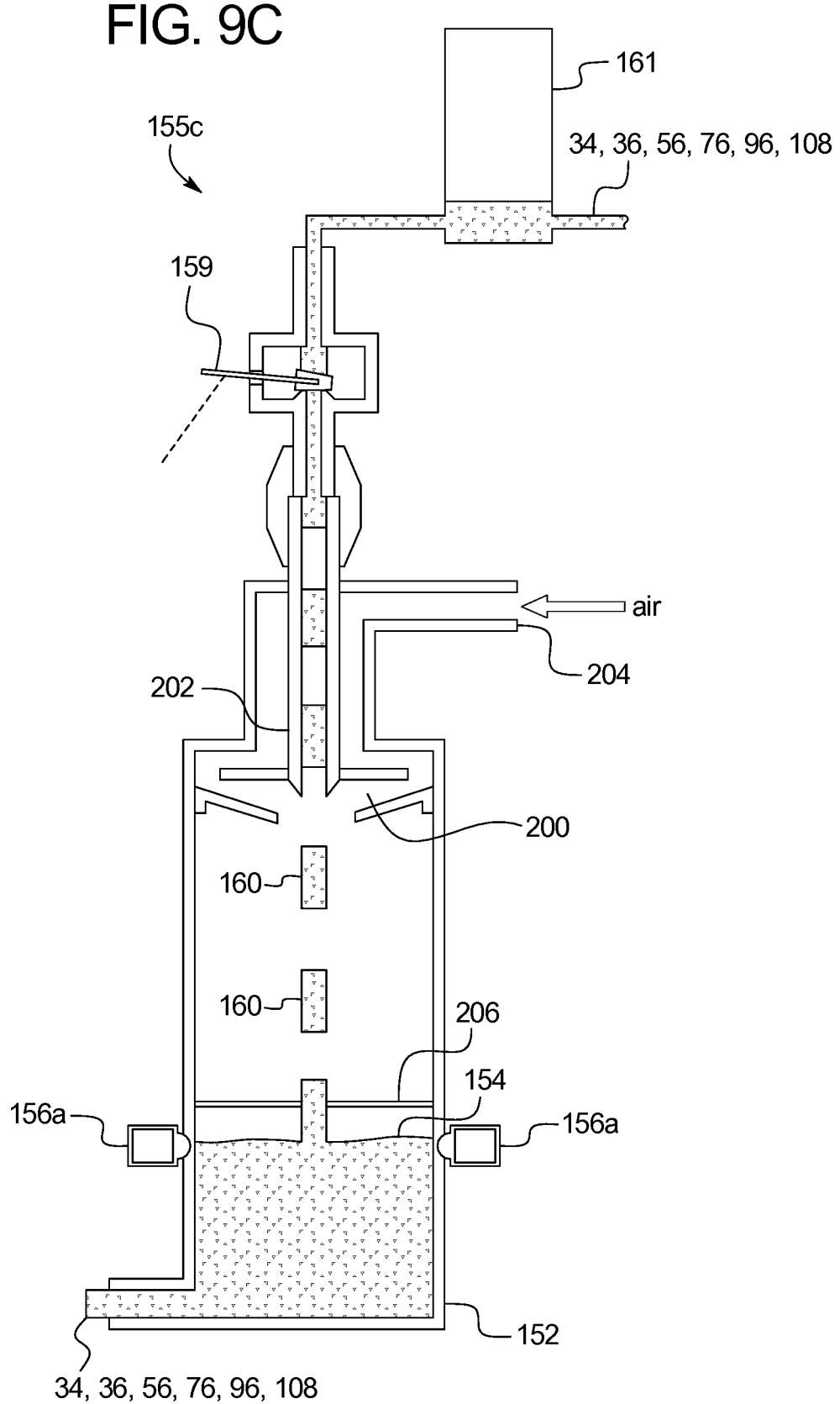
FIG. 9C is a sectioned elevation view of yet another embodiment of a flow path insulator of the present disclosure, which provides a third example for creating liquid segments in combination with the use of an air isolation chamber to help maintain an environment conducive to forming and maintaining the segments.

Flow path insulator 155*c* of FIG. 9C illustrates still another embodiment for creating drops or segments 160 in combination with the operation of air isolation chamber 200. Flow path insulator 155*c* includes all of the structure, functionality and alternatives discussed herein for line 34, 36, 76, 56, 96 or 108, container 152, liquid/air interface 154, level sensors 156*a*/156*b*, air isolation chamber 200, and air inlet line 204. Flow path insulator 155*c* also includes a two-way valve 159 under control of logic implementer 20 and a compliance chamber 161 for filling and emptying with fluid. Logic implementer 20 causes two-way valve 159 to open and close to split the water, blood, or dialysis fluid into fluid segments 160 exiting at nozzle end 202 of the passage. Two-way valve 159 may be an electrically actuated solenoid valve, for example. Compliance chamber 161 fills with fluid when two-way valve 159 is closed and drains fluid when two-way valve 159 is open. In this manner, the closing of valve 159 does not build pressure in line 34, 36, 76, 56, 96 or 108. Air isolation chamber 200 surrounds fluid segments 160 exiting nozzle end 202 so as to maintain the spaces between segments 160 in a dry and non-conductive state.

Figure 9D:
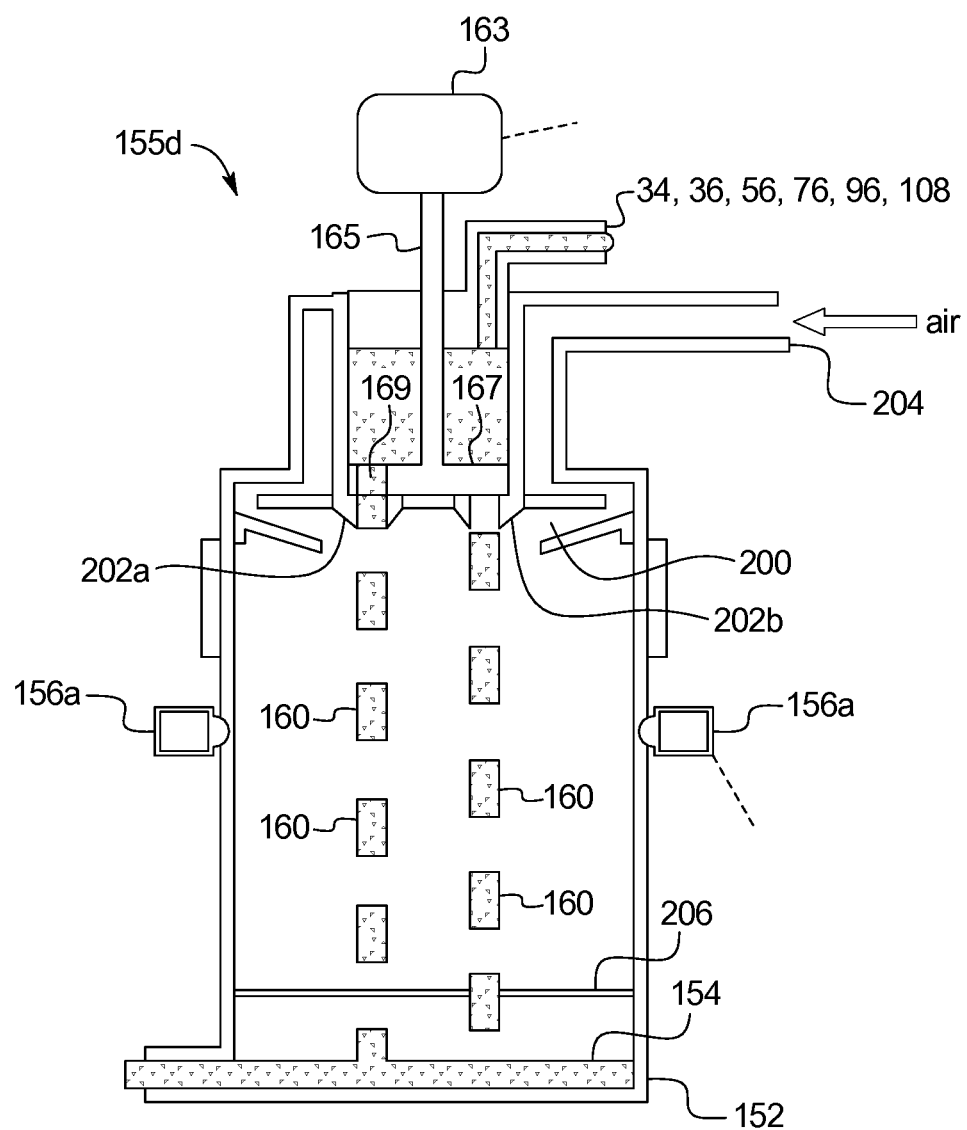
FIG. 9D is a sectioned elevation view of yet a further embodiment of a flow path insulator of the present disclosure, which provides a fourth example for creating liquid segments in combination with the use of an air isolation chamber to help maintain an environment conducive to forming and maintaining the segments.

Flow path insulator 155*d* of FIG. 9D illustrates a further embodiment for creating drops or segments 160 in connection with air isolation chamber 200. Flow path insulator 155*d* includes all of the structure, functionality and alternatives discussed herein for line 34, 36, 76, 56, 96 or 108, container 152, liquid/air interface 154, level sensors 156*a*/156*b*, air isolation chamber 200, and air inlet line 204. Flow path insulator 155*d* also includes a motor 163, e.g., an electric motor, under control of logic implementer 20. Motor 163 rotates a shaft 165, which is connected to a flange 167 defining one or more hole or aperture 169. Logic implementer 20 causes motor 163 to spin flange 167 at a desired angular velocity to cause the one or more hole or aperture 169 to align with one or more nozzle end 202*a*, 202*b* of air isolation chamber 200 at a desired frequency to create a desired number and size of water, blood, or dialysis fluid segments 160, which exit at nozzle ends 202*a*, 202*b*. Shaft 165 and flange 167 are made of a medically and physiologically safe metal, plastic and/or rubber, so they may contact the water, blood, or dialysis fluid safely. Air isolation chamber surrounds fluid segments 160 exiting nozzle ends 202*a*, 202*b* so as to maintain the spaces between segments 160 dry and non-conductive.

As discussed above, air, e.g., pressurized air, may be provided during treatment to keep air isolation chamber 200 dry and with low humidity. Between treatments, system 10 may run a cleaning procedure in which hot, fresh water with or without a cleaning substance cleans both chambers 200 and 212 of flow path insulators 155. The fresh water dissolves salt deposits located within lower chamber 212 (and any unlikely deposits that may form in air isolation chamber 200). The heat and/or cleaning agent battle such biological deposits.

Figure 10:
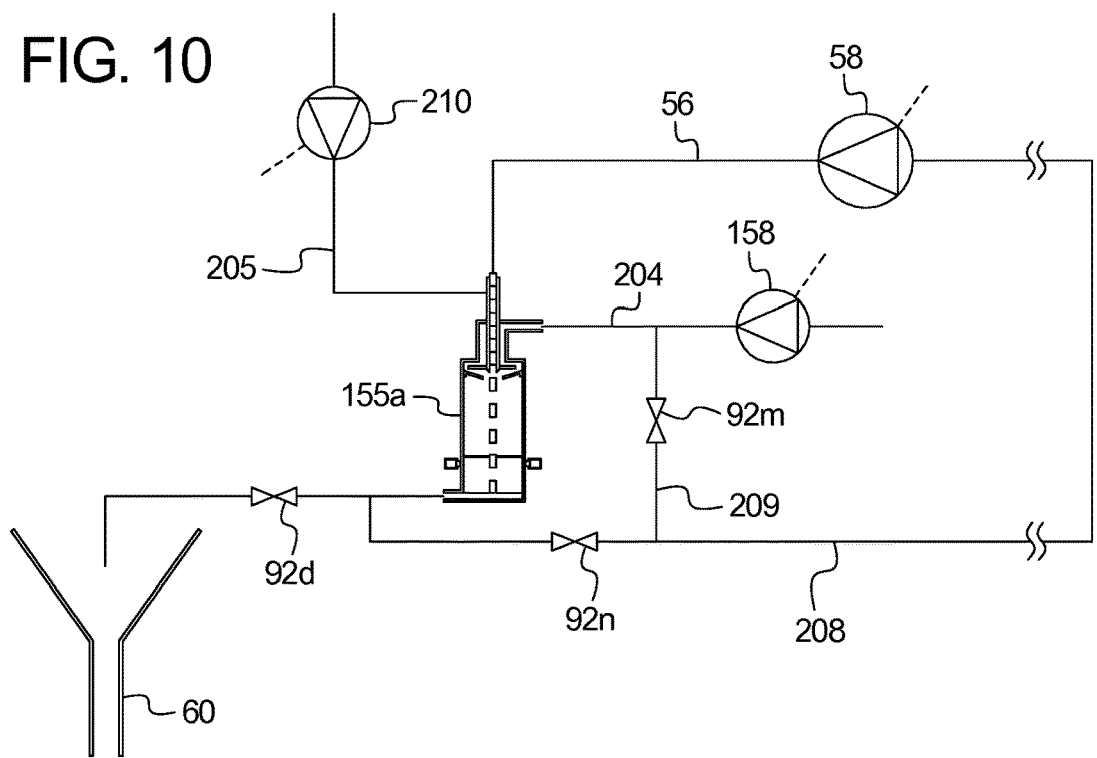
FIG. 10 is a flow schematic illustrating one possible way to perform treatment and then disinfect the same circuit using the flow path insulator of FIG. 9A, for example.

FIG. 10 illustrates one example for placing a flow path insulator, such as flow path insulator 155*a* (FIG. 9A) in used dialysis fluid and drain line 56, which operates with used dialysis fluid pump 58 under control of logic implementer 20 and a recirculation line 208. As discussed above, used dialysis fluid pump 58 during regular treatment pumps used dialysis fluid through used dialysis fluid and drain line 56 to drain 60. Used dialysis fluid and drain line 56 together with recirculation line 208 and a bypass line 209 provide a recirculation loop in which hot water/agent cleaning fluid may be recirculated between treatments to clean and flush those lines as well as other lines within dialysis fluid circuit 30.

In FIG. 10, drain valve 92*d* and recirculation valves 92*m* and 92*n*, each under control of logic implementer 20, are controlled differently depending upon whether machine 12 is delivering treatment or providing disinfection. During treatment, logic implementer 20 closes recirculation valves 92*m* and 92*n* and opens drain valve 92*d*. Logic implementer 20 during treatment also causes used dialysis fluid pump 58 to pump used dialysis fluid through flow path insulator 155*a* to drain 60. Logic implementer 20 during treatment further causes air pumps 158 and 210, e.g., volumetric air pumps, to pump air into different places within flow path insulator 155*a* via lines 204 and 205 respectively. Air pump 158 pumps dry and perhaps heated air via line 204 into air isolation chamber 200 to keep the spaces between flow segments 160 dry and non-conductive as has been discussed herein. Logic implementer 20 may control first air pump 158 to pump air constantly into air isolation chamber 200. Second air pump 210 on the other hand pumps air, which may be dry air, but it is not as critical to be dry or as dry, via line 205 into used dialysis fluid and drain line 56 to create flow segments 160 in the first place, as discussed above with FIG. 9A. In particular, logic implementer 20 may control air pump 210 to produce short bursts of air that interrupt the used dialysis fluid flow, causing the formation of fluid segments 160.

During disinfection or recirculation, logic implementer 20 opens recirculation valves 92*m* and 92*n* and closes drain valve 92*d*. Logic implementer 20 causes used dialysis fluid pump 58 to circulate heated water and/or cleaning solution through used dialysis fluid and drain line 56, flow path insulator 155a including air isolation chamber 200, recirculation line 208, bypass line 209, and air lines 204 and 205. After cleaning fluid is pumped through flow path insulator 155a and lines 56, 204, 208 and 209, logic implementer 20 causes system 10 to pump reverse osmosis ("RO") purified water through flow path insulator 155a and lines 56, 204, 208 and 209 to remove any conductive fluid from insulator 155a and the lines to drain 60 via opened drain valve 92d. After the RO water rinse, one or both air pumps 158 and 210 may pump air through flow path insulator 155a and the lines to dry the lines and insulator 155a. The above-described cleaning process ensures that flow path insulator 155a (or any of the insulators 155 or insulators 150 operating with air isolation chamber 200) is pristinely clean before each treatment using system 10.

Figure 11:
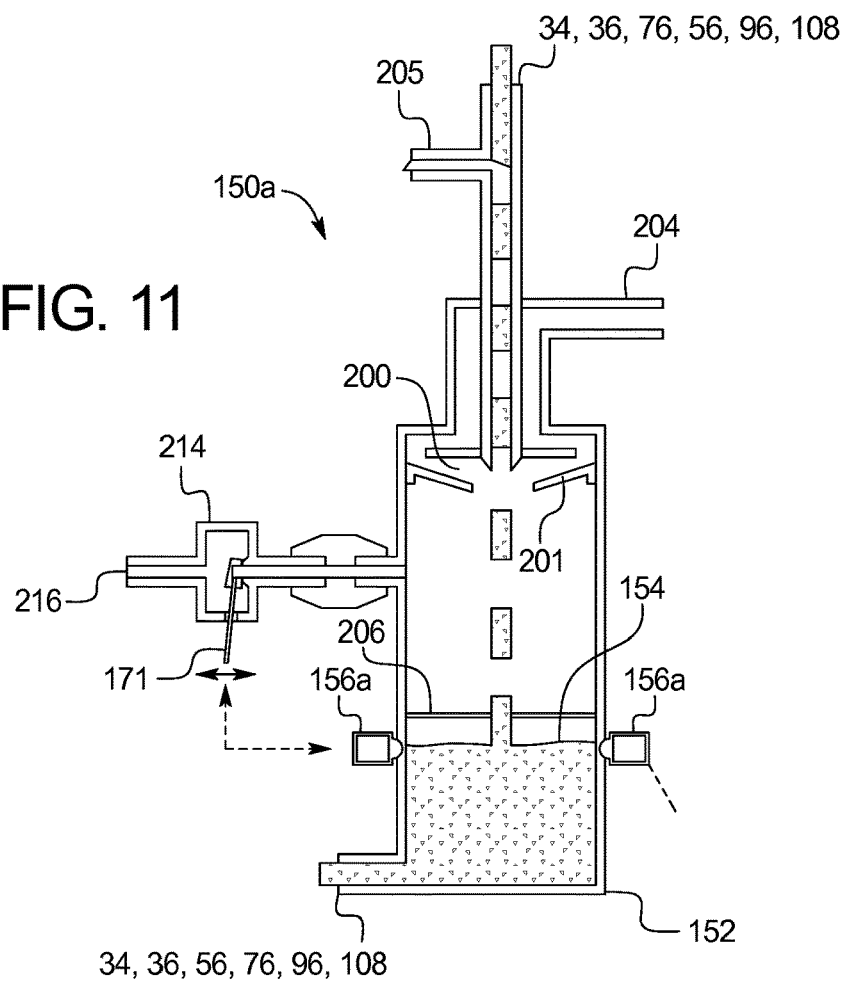
FIG. 11 is a sectioned elevation view of the flow path insulator of FIG. 9A, showing an additional vent and vent valve possible with any of the flow path insulators of the present disclosure.

Air may vent through used dialysis fluid and drain line 56 to drain 60 as has been described herein, or alternatively out a separate alternative air port 214 illustrated in FIG. 11. The alternative flow path insulator 155a in FIG. 11 includes an air port 214 located beneath one or more baffle 201 defining air isolation chamber 200. Air port 214 in the illustrated embodiment includes a hydrophobic cover or vent 216, which (i) filters any air entering container 152 and (ii) prevents any liquid including disinfecting hot water or hot water with disinfectant from escaping container 152 though port 214. Optical sensors 156a, for example, may be used with logic implementer 20, which also controls an air valve 171 to maintain a desired level for liquid/air interface 154 within chamber 212.

In particular, FIG. 11 illustrates that a signal from sensor pair 156a may be fed to logic implementer 20, which in turn controls an air valve 171 to either allow or not allow air to dissipate through cover or vent 216. Any of flow path insulators 150 or 155 may employ air port 214, vent 216, and liquid level air valve 171. In an embodiment, when sensor pair 156a does not see liquid, its output to logic implementer 20 is indicative of a no liquid sensed, which causes logic implementer 20 to open valve 171 to allow air to exit through vent 216, releasing air pressure within container 152, which allows liquid level 154 to rise within container 152 to the height of sensor pair 156a. When the liquid level 154 rises to the height of sensor pair 156a, the output of sensor pair 156a switches to being indicative of liquid being sensed, which causes logic implementer 20 to close valve 171 to disallow air from exiting through vent 216, building air pressure within container 152, and causing liquid level 154 to fall below the level of sensor pair 156a. The above cycle is then repeated.

Referring again to FIG. 1B, FIG. 1B illustrates another feedback embodiment or testing apparatus for any of the flow path insulators 150, 155 described herein, which may be provided instead of the optical sensor drop or segment 160 analysis of FIG. 9A or in addition to the analysis of FIG. 9A. FIG. 1B shows a portion of the electrically floating dialysis fluid circuit 30 discussed above, and includes like element numbers for like components shown above in FIG. 1A. Flow path insulator 150, 155 located at the end of used dialysis fluid and drain line 56 receives air from air pump 158 as has been described herein. System 10 of FIG. 1B is electrically floating in the dialysis fluid circuit 30 to the right of flow path insulator 150, 155, blood set 100 and dialyzer 102 to ensure that there is no path to earth ground 226 to the right of flow path insulator 150, 155, blood set 100 and dialyzer 102. It is assumed that used dialysis fluid and drain line 56 to the left of flow path insulator 150, 155 is connected to earth ground as indicated by the earth ground symbol 226 between valve 92d and flow path insulator 150 in FIG. 1B. Flow path insulator 150, 155 breaks the path to earth ground 226 via drain 60 located outside of machine 12.

To ensure that the electrically floating pathways and the flow path insulator 150, 155 are working properly, system 10 of FIG. 1B provides a leakage current monitoring device 220. Leakage current monitoring device 220 provides an current generator 222 in electrical communication with used dialysis fluid and drain line 56 (or alternatively with fresh dialysis fluid line 76, or alternatively with electrical bypass line 250 conducting electricity between fresh dialysis fluid line 76 and used dialysis fluid and drain line 56). Current generator 222 may be connected to used dialysis fluid and drain line 56 (or lines 76 or 250) via first and second conductive couplers (e.g., including stainless steel, conductive polymer or conductive carbon) placed in the liquid line. Current generator 222 is connected via a three-position switch 224 to either earth ground 226, a disconnected (analogous to neutral) position, or to a fluid path (analogous to line) position, respectively. When switch 224 is connected to the fluid path (analogous to line) position, a voltage meter 228 may read the voltage generated by current generator 222. When switch 224 is in the disconnected position (analogous to neutral), connection to earth ground 226 is not made, current source 222 does not generate current in dialysis fluid circuit 30, however, voltage meter 228 may read a voltage in the dialysis circuit. When switch 224 is connected to ground, logic implementer 20 looks for a fault voltage sensed by voltage meter 228, which is generated within system 10 to the right of flow path insulator 150, 155, indicating that system 10 is not operating properly.

When switch 224 is connected to ground, the current may be split between current through flow path resistor 230 and drain line 56, wherein the split ratio is dependent on the relative impedances. System 10 in an alternative embodiment adds an extra switch to ground for the fluid path downstream of flow path resistor 230 and upstream of flow path insulator 150, 155. The extra switch provides an opportunity to test for currents generated by system 10 to the right of leakage current monitoring device 220. The current generator may also be designed to generate current at several frequencies (could also include DC) to differentiate between different sources of currents (generated or from other sources). The sensitivity to current for the human body decreases with frequency.

In one embodiment, current monitoring device 220 tests system 10 in FIG. 1B initially before the patient is connected to the dialysis machine 12. Logic implementer 20 causes switch 224 to close towards protective earth 226. Here, current may flow from current generator 222 through the portion of used dialysis fluid and drain line 56 in parallel with current generator 222 (called a "flow path resistor" 230, which is a resistance/impedance over a portion of used dialysis fluid and drain line 56 filled with dialysis fluid) to protective earth 226. This test should accordingly only be done when the patient is well shielded from machine 12 (e.g., patient is not connected to machine 12 or the patient is connected to blood lines 106, 108, but is isolated from machine 12 via a stopped blood pump 120 and closed blood line valves and/or clamps). If the electrically floating dialysis fluid circuit 30, blood set 100 and dialyzer 102 and flow path insulator 150, 155 are working well, there will be minimal or no current and measured voltage (or no measured voltage) at voltage meter 228 over the "flow path resistor 230". The voltage measured and sent to logic implementer 20 should be close to or at zero. If so, logic implementer 20 allows the patient to proceed with treatment.

If not, logic implementer 20 causes user interface 14 to produce an audio, visual or audiovisual alarm indicating that there is an issue with the machine's electrical insulation.

With the patient still isolated from the machine, logic implementer 20 then causes switch 224 to move to its upper fluid path (analogous to line) position, so that voltage meter 228 may read the voltage generated by the current from current generator 222. For example, current generator 222 may be a ten or fifty microampere (µA) current source, which is an upper limit for cardiac voltage or body floating devices. Voltage meter 228 will then read the voltage generated by the ten or fifty microamperes (µA) from current generator 222 over the flow path resistor 230. The voltage value generated is sent to and stored at logic implementer 20.

When moving towards treatment, logic implementer 20 causes switch 224 to move to its disconnected (analogous to neutral) position, so that floating dialysis fluid circuit 30, blood set 100 and dialyzer 102 are floating fully and are not intentionally connected to any protective earth 226. When the patient is connected to machine 12, logic implementer monitors voltage meter 228 over the course of treatment. Voltage meter 228 during treatment measures any leakage current voltage generated across flow path resistor 230. Logic implementer 20 compares the measured voltage to the stored line test voltage from the current generator 222 test discussed above (corresponding to the acceptable limits for cardiac floating and body floating). If the in-treatment measured voltage is below the stored line test voltage (e.g., by an engineering or safety factor), logic implementer 20 allows the patient to continue with treatment. If the measured in-treatment voltage is at or above the stored line test voltage (or above an engineering or safety factor thereof), logic implementer 20 causes machine 12 to stop and user interface 14 to produce an audio, visual or audiovisual alarm indicating that there is an issue with the machine's electrical insulation. In one embodiment, logic implementer 20 causes blood pump 120 to stop and line the clamps along blood set 100 to close to enlarge any possible impedance towards protective earth 126, thereby mitigating the fault currents, and reducing any potentially dangerous current to the patient.

The advantages of system 10 in FIG. 1B are: (i) it may be able to test that the fluid flow insulator 150, 155 and the electrically floating pathways are working, (ii) it may be able to test that no dangerous current is flowing through flow path resistor 230 during treatment, (iii) it may be able to place protective earth 226 at outlet of machine, decoupled from drain 60. It should also be appreciated that FIG. 1B shows one example placement of current monitoring device 220, however, current monitoring device 220 may be placed anywhere, to test any one or more fluid flow insulator 150, 155 of the present disclosure, including a fluid flow insulator 150, 155 located outside the machine in FIGS. 12A and 12B, and including placement in blood set 100 (which may require the addition of conductive contacts in the blood set).

In an alternative embodiment, earth ground 226 due to drain 60 is used for the ground position of switch 224 instead of the separate earth ground 226 illustrated in FIG. 1B. Here, a short cut wire (not illustrated) extends from switch 224 over to earth ground 226 at drain 60, located, e.g., between valve 92d and flow path insulator 150. In this alternative embodiment, the advantage (iii) listed above would not exist, however, this alternative may also provide information concerning the earth ground 226 due to drain 60. Further alternatively, current source 222 may be a voltage source and/or voltage meter 228 may be a current meter.

Figure 12C:
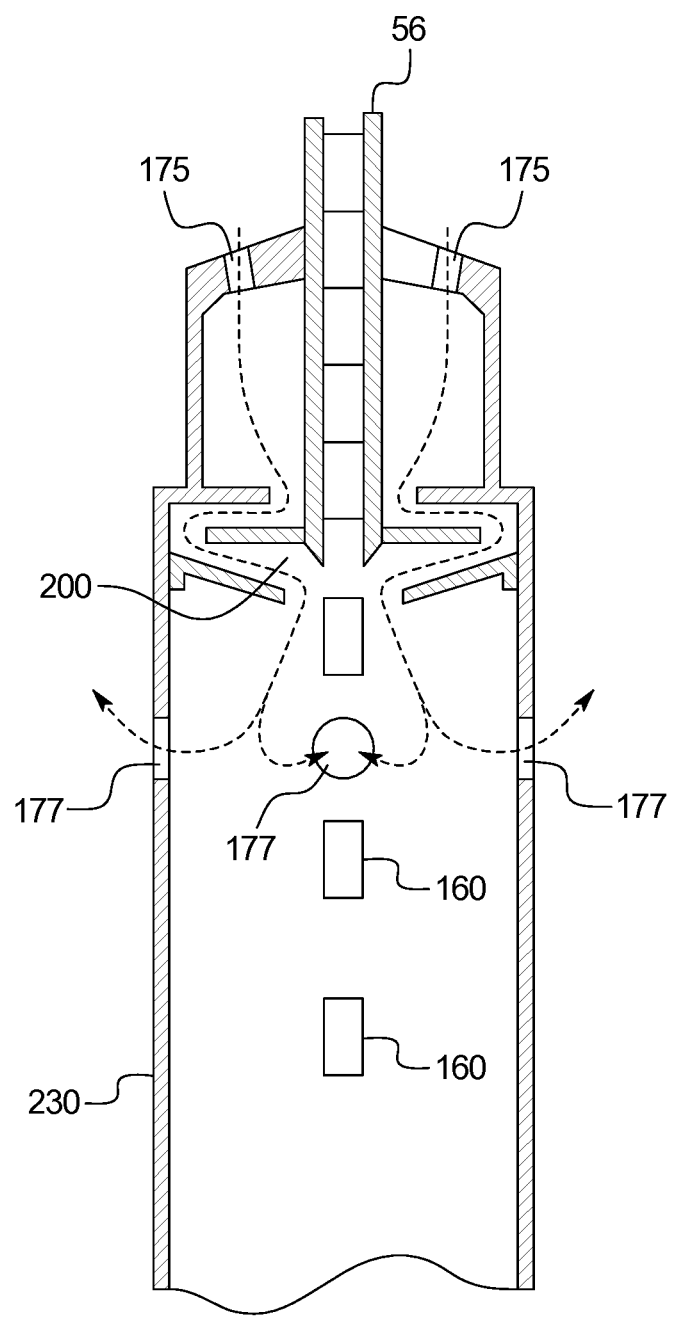
FIG. 12C is a sectioned elevation view of a flow path insulator showing how any of the flow path insulators described herein may be configured to draw air into its air separation chamber, as opposed to using forced or pressurized air.

Referring now to FIGS. 12A to 12C, various embodiments for providing a flow path insulator 150, 155 (insulator 155 is illustrated) outside of machine housing 12 are illustrated, which may be implemented alone or in combination with one or more insulator 150, 155 located inside of machine 12. The outside flow path insulator 150, 155 may be made more cost effectively because an enclosed liquid container 152 is not needed. It is also easier for one to remove and exchange outside flow path insulator 150, 155 for cleaning or replacement. Liquid/air interface 154 may be located instead in drain 60. A splashguard 206 described above in connection with FIG. 9A may also be located in drain 60 (FIG. 12A) and/or within tube 230 (FIG. 12B) of flow path insulators 150, 155. Outside flow path insulators 150, 155 may accordingly include a simple tube 230, which as illustrated may be open at its lower end. Open tube 230 to atmosphere should be less humid on the inside than the enclosed insulators 150, 155 located within machine 12. Tube 230 should therefore be less prone to producing the unwanted conductive connection between liquid/air interface 154 and used dialysis fluid within used dialysis fluid and drain line 56. Tube 230 should also be easy to flush and disinfect, and may in an embodiment be a disposable component of system 10. Likewise, air line 204 located outside of machine 12 may be flushed and disinfected from within machine 12. Tube 230 may operate with any of liquid level sensors or drop monitoring sensors 156 (e.g., 156a or 156b) discussed herein. Another advantage of outside flow path insulator 150, 155 is that it is positioned outside machine 12 in direct alignment with drain 60, where it may be removed and cleaned easily, e.g., in a standard dishwasher, and returned quickly to service at machine 12.

Outside flow path insulator 155 in FIG. 12A operates very similar to flow path insulator 155c illustrated in FIG. 9C. Both use a two-way valve 159 in the liquid line under control of logic implementer 20 and a compliance chamber 161 for filling and emptying with liquid. Logic implementer 20 again causes two-way valve 159 to open and close to split the water, blood, or dialysis fluid into fluid segments 160 exiting within air isolation chamber 200. Two-way valve 159 may be an electrically actuated solenoid valve, for example. Compliance chamber 161 fills with fluid when two-way valve 159 is closed and drains fluid when two-way valve 159 is open. In this manner, the closing of valve 159 does not build pressure in used dialysis fluid and drain line 56 upstream of valve 159. Air isolation chamber 200 surrounds the exiting fluid segments 160 so as to maintain the spaces between segments 160 in a dry and non-conductive state.

Outside flow path insulator 155 in FIG. 12B operates very similar to flow path insulator 155a illustrated in FIGS. 9A, 10 and 11. Each use a first air pump 158 and first air line 204 to create a dry environment within air isolation chamber 200 and a second air pump 210 and a second air line 205 to provide bursts of air to separate liquid, e.g., used dialysis fluid flow within used dialysis fluid and drain line 56, into segments 160. Again, air isolation chamber 200 surrounds the exiting fluid segments 160 so as to maintain the spaces between segments 160 in a dry and non-conductive state.

FIG. 12C illustrates that the outside flow path insulators 155 may define or provide one or more air opening or port 175 that allows air to enter and one or more opening or port 177 that allows air to escape as liquid segments 160 fall through tube 230. Segments 160 will pull air with them and create airstreams from the openings or ports 175 of the insulator 155 as illustrated via the dotted line in FIG. 12C. Liquid segments 160 will drive air flow in this way. The amount or flowrate of air that will be pulled by liquid segments 160 may be influenced by design. Although not illustrated, opening or port 175 into outside flow path insulator 155 may be in the form of one or more venturi nozzle, which uses the continuous flow through a column of fluid just prior to the segments 160 being formed to suck a controlled amount of air into air isolation chamber 200. In any case, in FIG. 12C pressurized air is advantageously not needed to maintain a dry air isolation chamber 200 of outside flow path insulator 155 dry.

It should be appreciated that in alternative embodiments, e.g., in combination with the electrically floating fluid pathway described above, that only one of outside or inside flow path insulator 150, 155 in FIGS. 12A to 12C need be provided. Providing only outside flow path insulator 150, 155 in combination with a properly electrically floating fluid pathway is advantageous for a number of reasons. First, pressurized air is not needed, reducing cost and complexity. Second, tube 230 for the outside flow path insulator 150, 155 may be made as large as needed to also help prevent electrical creep and static discharge. Third, the chassis for machine 12 does not have to be made larger to accommodate the potentially large outside flow path insulator 150, 155. Fourth, the outside flow path insulator 150, 155 is easily removed, cleaned and replaced as discussed above.

It should be understood that various changes and modifications to the presently preferred embodiments described herein will be apparent to those skilled in the art. Such changes and modifications may be made without departing from the spirit and scope of the present invention and without diminishing its intended advantages. It is therefore intended that such changes and modifications be covered by the appended claims.

The invention is claimed as follows:

1. A renal failure therapy system comprising:
   a dialyzer;
   a blood circuit including a blood pump in fluid communication with the dialyzer;
   a dialysis circuit in fluid communication with the dialyzer; and
   at least one flow path insulator located in the dialysis circuit or the blood circuit, the flow path insulator including (i) a structure that separates liquid flowing within the flow path insulator into a plurality of separated liquid segments that create electrical isolation within the flow path insulator, and (ii) an air isolation chamber that is separated by at least one baffle from a lower chamber that receives the liquid segments to keep the air isolation chamber dry.

2. The renal failure therapy system of claim 1, wherein the structure that separates liquid flowing within the flow path insulator into a plurality of separated liquid segments is located above the at least one baffle, and the lower chamber is located below the at least one baffle and the air isolation chamber.

3. The renal failure therapy system of claim 1, wherein the flow path insulator is configured and arranged to use a flow of separated liquid segments to pull air through the air isolation chamber.

4. The renal failure therapy system of claim 1, wherein the flow path insulator includes an inlet, wherein the air isolation chamber surrounds the inlet, and which further includes an air pump positioned and arranged to pressurize air within the air isolation chamber.

5. The renal failure therapy system of claim 1, wherein the structure that separates liquid flowing within the flow path insulator into liquid segments includes at least one valve opened and closed sequentially to create the liquid segments.

6. The renal failure therapy system of claim 1, wherein the structure that separates liquid flowing within the insulator into liquid segments includes a turbine wheel including blades that are spun by the flowing liquid.

7. The renal failure therapy system of claim 1, wherein the structure that separates liquid flowing within the insulator into liquid segments includes a manifold plate defining a plurality of apertures, each aperture restricting the flowing liquid.

8. The renal failure therapy system of claim 1, wherein the structure that separates liquid flowing within the insulator into liquid segments includes a wheel having a plurality of receptacles that fill individually, wherein the weight of the filled receptacles causes the wheel to turn.

9. The renal failure therapy system of claim 1, which includes a logic implementer, wherein the flow path insulator includes a level sensor configured to send an output to the logic implementer, the logic implementer using the output to control an air pump to achieve a desired liquid level in the insulator.

10. The renal failure therapy system of claim 1, which includes at least one testing apparatus for testing whether the flow path insulator is operating properly.

11. The renal failure therapy system of claim 10, wherein the at least one testing apparatus includes a sensor positioned and arranged to sense whether the fluid segments are being formed properly.

12. The renal failure therapy system of claim 10, wherein the at least one testing apparatus includes a voltage or current meter positioned and arranged to detect voltage or current in the dialysis circuit.

13. The renal failure therapy system of claim 1, wherein the dialysis circuit includes a fresh dialysis fluid line and a used dialysis fluid line, and which includes a first flow path insulator located in the fresh dialysis fluid line and a second flow path insulator located in the used dialysis fluid line.

14. The renal failure therapy system of claim 13, wherein the first flow path insulator is located between a furthest downstream flow component in the fresh dialysis fluid line and the dialyzer, and the second flow path insulator is located between a furthest upstream flow component in the used dialysis fluid line and the dialyzer.

15. The renal failure therapy system of claim 1, wherein the flow path insulator is placed at the drain of the dialysis circuit and/or outside of a machine housing holding the dialysis circuit.

16. The renal failure therapy system of claim 15, wherein at least one concentrate container is suspended off of the ground or provided with standoffs to preclude a capacitive coupling with the ground.

17. The renal failure therapy system of claim 1, wherein the flow path insulator is placed in a concentrate line of the dialysis circuit or in the blood circuit.

18. The renal failure therapy system of claim 1, wherein the flow path insulator uses a pulsed source of air to create separated liquid segments.

19. A renal failure therapy machine comprising:
   a dialyzer;
   a blood circuit including a blood pump in fluid communication with the dialyzer;
   a dialysis circuit in fluid communication with the dialyzer;
   at least one flow path insulator located in the dialysis circuit, the flow path insulator including a structure that separates liquid flowing within the flow path insulator into separated liquid segments that create electrical isolation within the flow path insulator; and an air pump positioned and arranged to pressurize air within an air isolation chamber of the flow path insulator.

20. The renal failure therapy machine of claim 19, wherein the flow path insulator is located at a downstream end of a used dialysis fluid and drain line of the dialysis circuit.

21. The renal failure therapy machine of claim 19, wherein the air isolation chamber encompasses an area of the flow path insulator at which the liquid segments are formed.

22. The renal failure therapy machine of claim 19, wherein the air isolation chamber is spaced away from a liquid/air interface formed within the flow path insulator.

23. The renal failure therapy machine of claim 19, wherein the air isolation chamber is part of a water or water and agent cleaning loop.

24. A renal failure therapy machine comprising:
a dialyzer;
a blood circuit including a blood pump in fluid communication with the dialyzer;
a dialysis circuit in fluid communication with the dialyzer, wherein the blood circuit, the dialyzer, and the dialysis circuit form an electrically floating fluid pathway in which the only electrical path to ground is via used dialysis fluid traveling through machine to earth ground, wherein the electrically floating fluid pathway includes at least one structure selected from the group consisting of: (i) an electrically bypassed sensor, (ii) at least one electrically insulated fluid component, and (iii) at least one electrically isolated signal line; and
at least one flow path insulator located at a drain end of the dialysis circuit, the flow path insulator including a structure that separates liquid flowing within the flow path insulator into separated liquid segments that create electrical isolation within the flow path insulator.

25. The renal failure therapy machine of claim 24, further comprising at least one testing apparatus for testing whether the flow path insulator is creating the electrical isolation properly, the at least one testing apparatus including a voltage or current meter and a switch that allows at least one selected from the group consisting of (i) a path to a ground position before treatment to test via the voltage or current meter whether the flow path insulator is creating the electrical isolation properly, and (ii) a path to a fluid path position to set a maximum voltage or current level before treatment, and a path to a disconnected position to test during treatment whether the flow path insulator is creating the electrical isolation properly based on the maximum voltage or current level.

26. A renal failure therapy system comprising:
a dialyzer;
a blood circuit including a blood pump in fluid communication with the dialyzer;
a dialysis circuit in fluid communication with the dialyzer;
at least one flow path insulator located in the blood circuit, the flow path insulator including a structure that separates liquid flowing within the flow path insulator into a plurality of separated liquid segments that create electrical isolation within the flow path insulator; and
a logic implementer programmed to operate a single needle treatment, the flow path insulator located in a single blood line of blood circuit running to a patient.

27. The renal failure therapy system of claim 26, further comprising at least one testing apparatus for testing whether the flow path insulator is creating the electrical isolation properly, the at least one testing apparatus including a voltage or current meter and a switch that allows at least one selected from the group consisting of (i) a path to a ground position before treatment to test via the voltage or current meter whether the flow path insulator is creating the electrical isolation properly, and (ii) a path to a fluid path position to set a maximum voltage or current level before treatment, and a path to a disconnected position to test during treatment whether the flow path insulator is creating the electrical isolation properly based on the maximum voltage or current level.

* * * * *